United States Patent [19]
Lin et al.

[11] Patent Number: 6,013,227
[45] Date of Patent: Jan. 11, 2000

[54] LUMEN DEVICE REPROCESSOR WITHOUT OCCLUSION

[75] Inventors: Szu-Min Lin, Laguna Hills; Paul Taylor Jacobs, Canyon, both of Calif.

[73] Assignee: Johnson & Johnson Medical, Inc., New Brunswick, N.J.

[21] Appl. No.: 08/992,602

[22] Filed: Dec. 17, 1997

[51] Int. Cl.[7] .................................................. A61L 2/18
[52] U.S. Cl. .......................... 422/28; 422/33; 422/292; 422/297; 422/300; 422/305
[58] Field of Search .................................. 422/20, 28, 31, 422/33, 292, 297, 298, 300, 305

[56] References Cited

U.S. PATENT DOCUMENTS

| | | | |
|---|---|---|---|
| 3,814,901 | 6/1974 | Morhack | 219/401 |
| 3,893,843 | 7/1975 | Fry et al. | 134/10 |
| 4,203,943 | 5/1980 | Gillis et al. | 422/27 |
| 4,321,232 | 3/1982 | Bithell | 422/23 |
| 4,337,223 | 6/1982 | Kaye | 422/112 |
| 4,380,530 | 4/1983 | Kaye | 422/300 |
| 4,410,492 | 10/1983 | Kaye | 422/27 |
| 4,576,792 | 3/1986 | Martensson | 422/27 |
| 4,579,597 | 4/1986 | Sasa et al. | 134/21 |
| 4,731,222 | 3/1988 | Kralovic et al. | 422/37 |
| 4,744,951 | 5/1988 | Cummings et al. | 422/28 |
| 4,756,882 | 7/1988 | Jacobs et al. | 422/23 |
| 4,892,706 | 1/1990 | Kralovic et al. | 422/28 |
| 4,937,046 | 6/1990 | Andersen et al. | 422/34 |
| 4,943,414 | 7/1990 | Jacobs et al. | 422/28 |
| 4,956,145 | 9/1990 | Cummings et al. | 422/28 |
| 5,017,241 | 5/1991 | Ryan | 134/22.12 |
| 5,037,623 | 8/1991 | Schneider et al. | 422/292 |
| 5,077,008 | 12/1991 | Kralovic et al. | 422/37 |
| 5,091,343 | 2/1992 | Schneider et al. | 422/297 |
| 5,114,596 | 5/1992 | Latterra | 210/798 |
| 5,116,575 | 5/1992 | Badertscher et al. | 422/28 |
| 5,186,893 | 2/1993 | Moulton et al. | 422/23 |
| 5,209,909 | 5/1993 | Siegel et al. | 422/292 |
| 5,217,698 | 6/1993 | Siegel et al. | 422/295 |
| 5,225,160 | 7/1993 | Sanford et al. | 422/28 |
| 5,260,021 | 11/1993 | Zeleznick | 422/28 |
| 5,266,275 | 11/1993 | Faddis | 422/116 |
| 5,279,799 | 1/1994 | Moser | 422/292 |

(List continued on next page.)

FOREIGN PATENT DOCUMENTS

| | | |
|---|---|---|
| 3416743 A1 | 7/1985 | Germany . |
| 63-302817 | 9/1988 | Japan . |
| WO 97/24147 | 7/1997 | WIPO . |

*Primary Examiner*—Elizabeth McKane
*Assistant Examiner*—Fariborz Moazzam
*Attorney, Agent, or Firm*—Knobbe, Martens, Olson & Bear, LLP

[57] ABSTRACT

A method for cleaning/sterilizing a device having a lumen with at least two open ends comprises the steps of: a) providing a container having at least one enclosure and at least one interface separating the enclosure from the container, the interface having at least one opening thereon, b) placing the device across the opening with one open end in the container and another open end in the enclosure, c) generating a flow of a cleaning solution through the lumen to clean the inner surface of the lumen, d) generating a flow of rinse solution through the lumen to rinse the inner surface of the lumen, e) treating the device with a chemical germicide, and f) adjusting the opening in any of steps c) to e) to reduce the areas on surface of the device occluded by contacting with the opening. An apparatus for cleaning/sterilizing a lumen device comprises a container having a fluid port for flowing and draining a fluid in and out the container. At least one enclosure is coupled with the container for receiving part of the lumen device so that one end of the lumen device is located in the enclosure and the other end of the lumen device is located in the container. An interface separates the container and enclosure. At least one openable and closable holder sealably is coupled to the interface. A source for creating a pressure difference between the container and the enclosure. A cleaning mechanism adapted to clean the device in the container or enclosure is also provided.

30 Claims, 17 Drawing Sheets

U.S. PATENT DOCUMENTS

| | | |
|---|---|---|
| 5,310,524 | 5/1994 | Campbell et al. ............... 422/33 |
| 5,348,711 | 9/1994 | Johnson et al. ............... 422/300 |
| 5,350,563 | 9/1994 | Kralovic et al. ............... 422/28 |
| 5,374,394 | 12/1994 | Kralovic ............... 422/28 |
| 5,391,360 | 2/1995 | Kochte et al. ............... 422/292 |
| 5,407,648 | 4/1995 | Allen et al. ............... 422/297 |
| 5,407,685 | 4/1995 | Malchesky et al. ............... 424/449 |
| 5,441,707 | 8/1995 | Lewis et al. ............... 422/300 |
| 5,443,801 | 8/1995 | Langford ............... 422/294 |
| 5,445,792 | 8/1995 | Rickloff et al. ............... 422/28 |
| 5,492,671 | 2/1996 | Krafft ............... 422/26 |
| 5,494,530 | 2/1996 | Graf ............... 134/18 |
| 5,505,218 | 4/1996 | Steinhauser et al. ............... 134/95.1 |
| 5,508,009 | 4/1996 | Rickloff et al. ............... 422/292 |
| 5,527,508 | 6/1996 | Childers et al. ............... 422/33 |
| 5,534,221 | 7/1996 | Hillebrenner et al. ............... 422/33 |
| 5,540,221 | 7/1996 | Riley ............... 422/300 |
| 5,552,115 | 9/1996 | Malchesky ............... 422/28 |
| 5,556,607 | 9/1996 | Childers et al. ............... 422/300 |
| 5,580,530 | 12/1996 | Kowatsch et al. ............... 422/102 |
| 5,609,821 | 3/1997 | Grimberg et al. ............... 422/28 |
| 5,641,464 | 6/1997 | Briggs, III et al. ............... 422/300 |
| 5,753,195 | 5/1998 | Langford et al. ............... 422/292 |
| 5,851,485 | 12/1998 | Lin et al. ............... 422/33 |
| 5,871,692 | 2/1999 | Haire et al. ............... 422/28 |

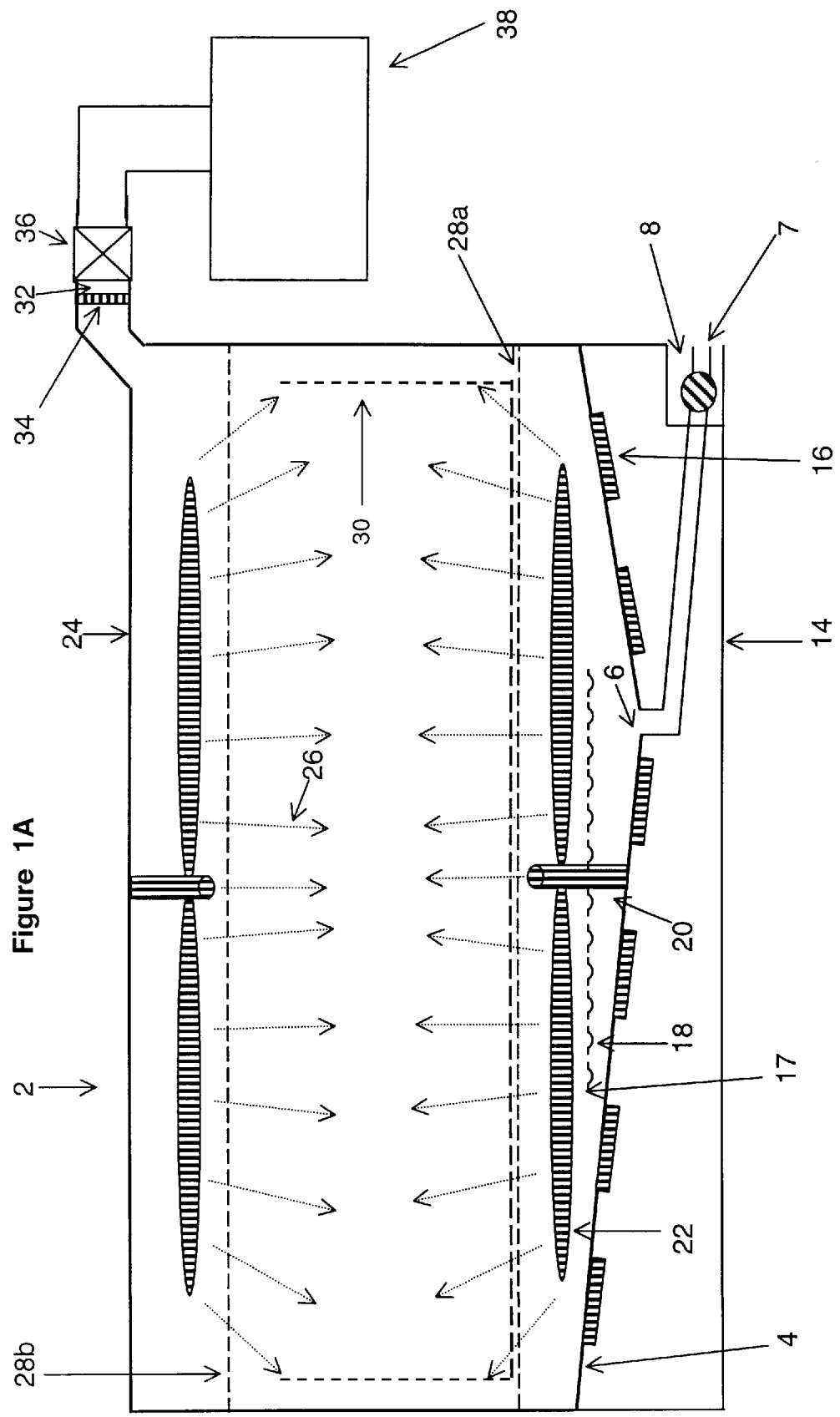

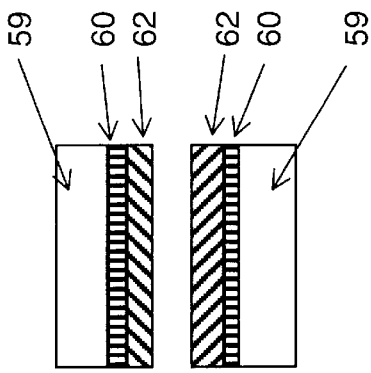
Figure 3F
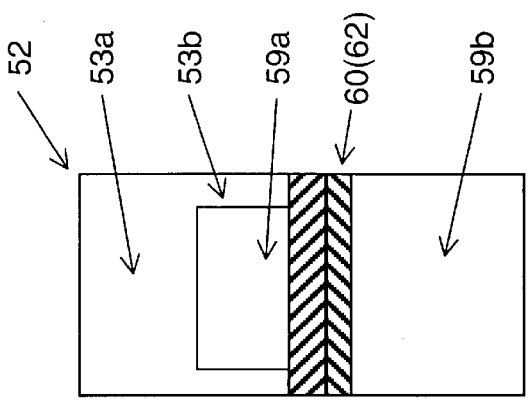
Figure 3G
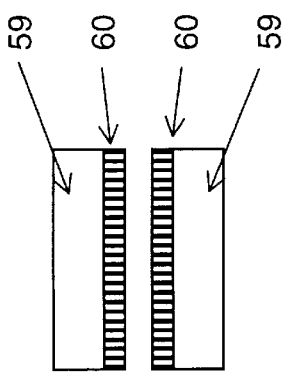
Figure 3D
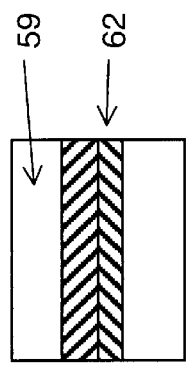
Figure 3E
Figure 3B
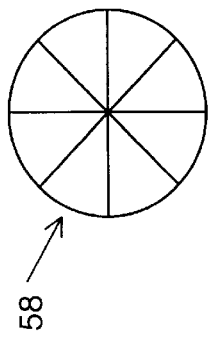
Figure 3C
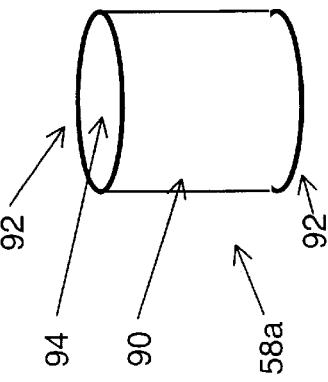

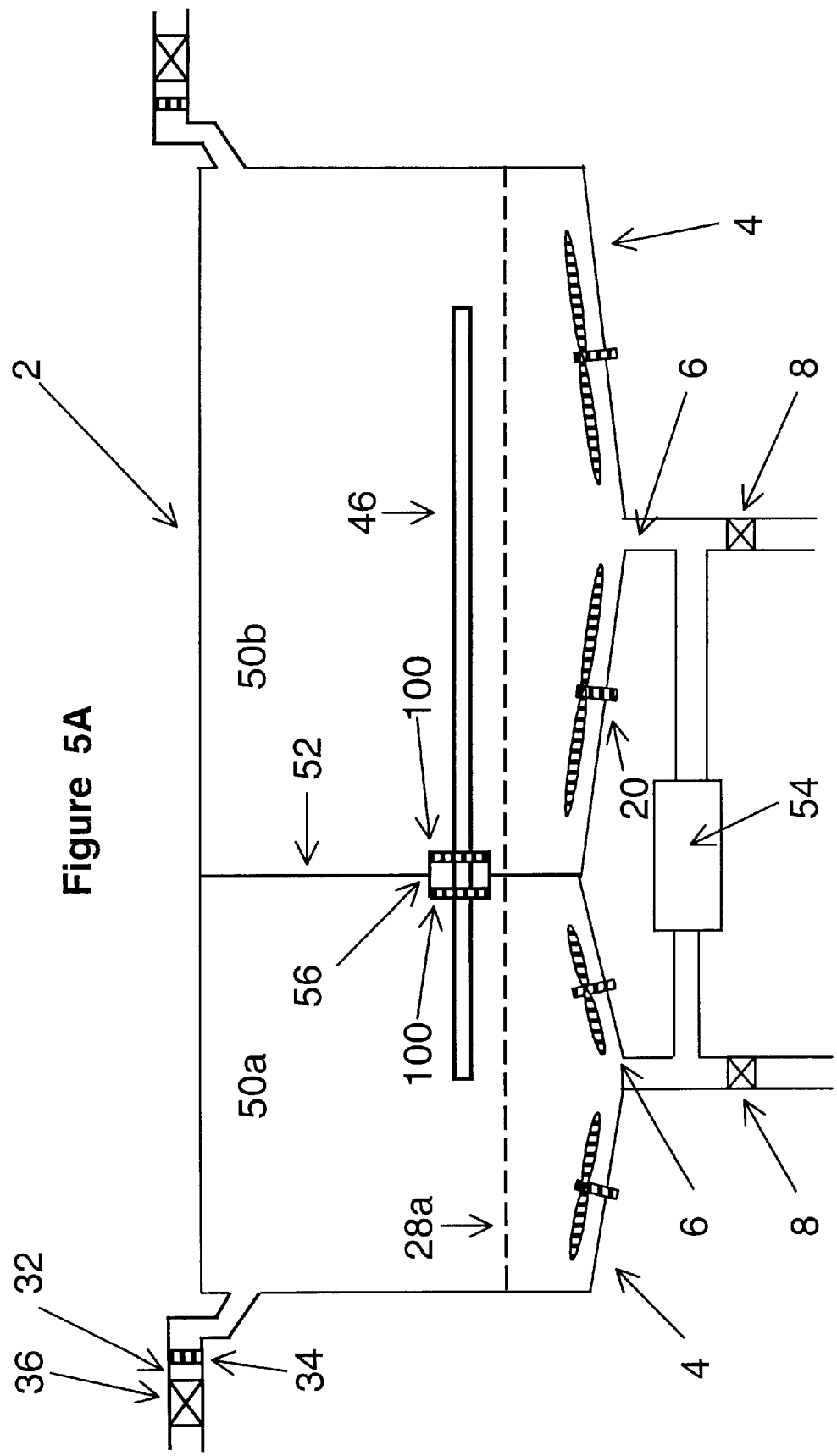

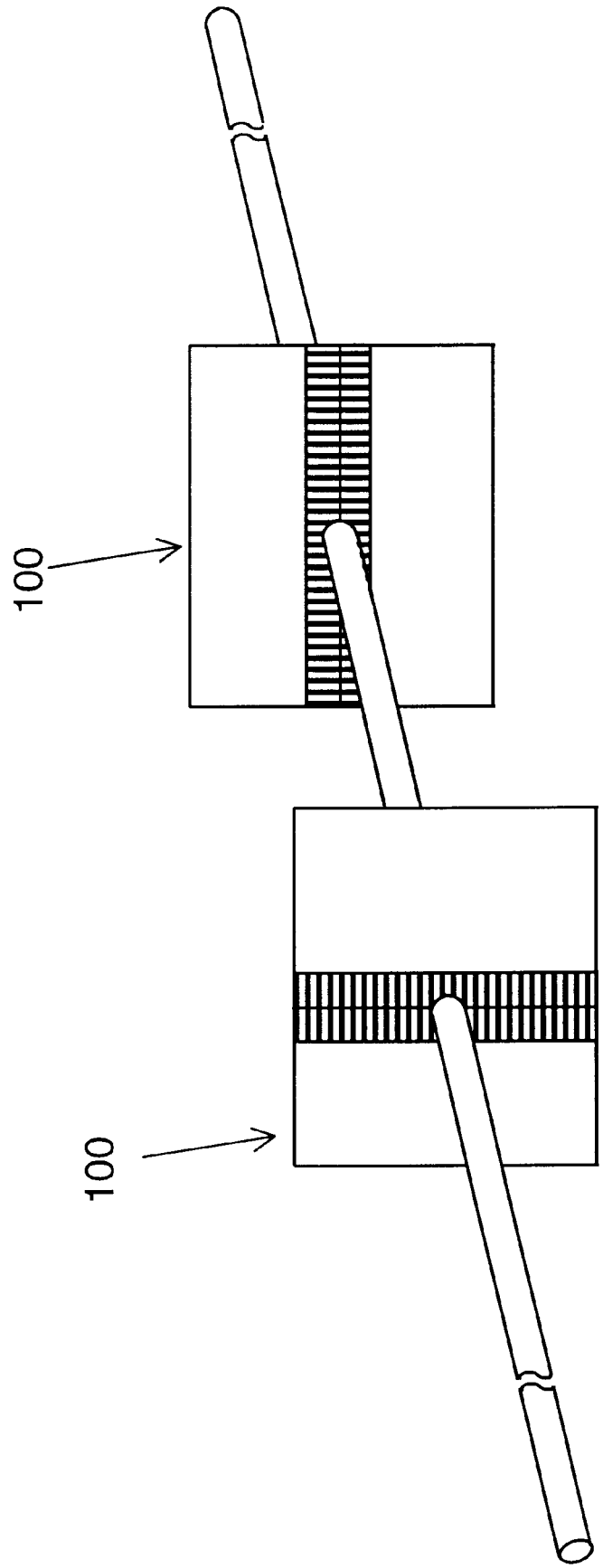

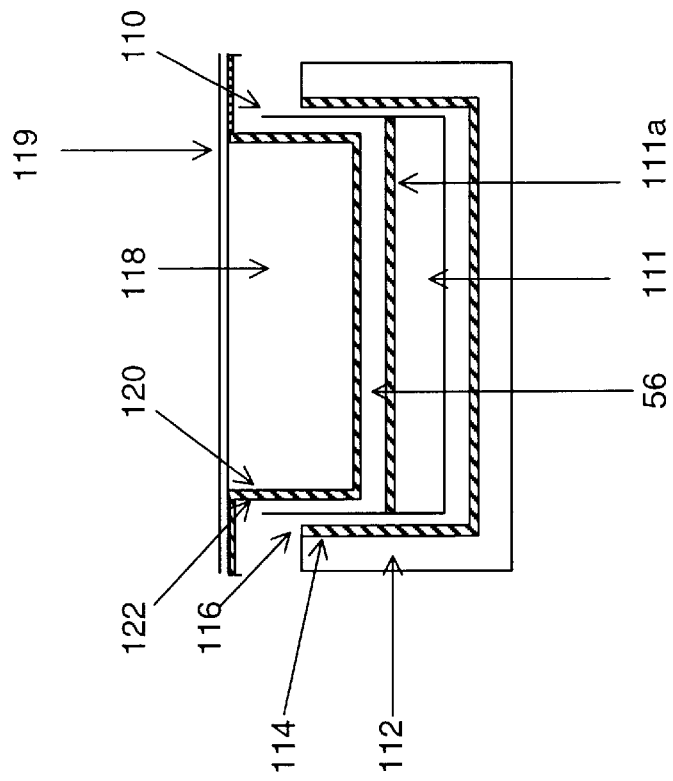
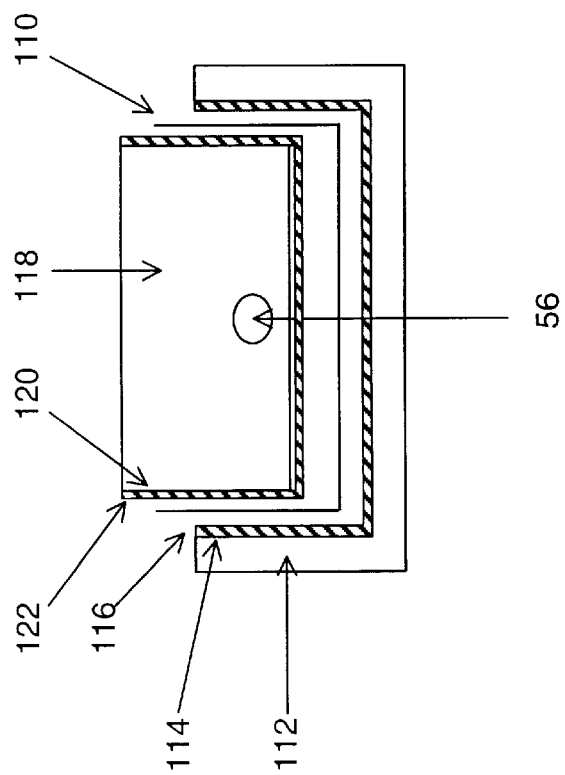

LUMEN DEVICE REPROCESSOR WITHOUT OCCLUSION

BACKGROUND OF THE INVENTION

This invention relates to systems and processes for cleaning, chemical sterilizing or disinfecting medical devices.

Medical instruments have traditionally been sterilized or disinfected using either heat such as is provided by steam, or a chemical in liquid, gas, or vapor state. Prior to sterilization or disinfection, the instruments to be treated are usually first cleaned and then sterilized or disinfected. After sterilization or disinfection with a liquid chemical germicide, purified water is used to rinse the instruments and then the instruments are dried. Numerous publications regarding the cleaning of medical devices and the sterilizing of medical devices are available.

U.S. Pat. No. 5,443,801 discloses a transportable cleaning/sterilizing apparatus and method for inside-outside washing and sterilization of medical/dental instruments. The apparatus functions in four sequential cycles: wash, rinse, sterilize, and dry. The sterilization step is conducted using ozonated and purified water, and the drying step is accomplished by injecting ozonated/deozonated sterile warm dry oxygen, or sterile inert gas into and exhausted from the wash chamber under a positive pressure relative to atmospheric. In this process, the device has to be rinsed with purified water after it is sterilized to remove sterilant residue before drying step.

U.S. Pat. No. 5,505,218 to Steinhauser et al. discloses a device for cleaning, disinfecting and maintaining medical or dental instruments. The device has a pot-shaped container with a multiplicity of mountings in the interior of the container each for one of tool holder, a water supply system, a compressed air supply system, and an ultrasonic transducer. The disinfection is conducted with heated water, and the drying is conducted with hot compressed air. This system is not designed for sterilization.

U.S. Pat. No. 5,279,799 to Moser et al. discloses apparatus for cleaning and testing endoscopes by injecting pressurized air into the sheath and pressurized air and washing liquid into the ducts. A washing chamber is provided which contains retractable cages to hold the endoscopes during cleaning and testing. This process includes washing, disinfecting, final rinsing with purified water, and air drying the ducts of a tubular article. A number of filters are involved in this system, and this system is not designed for sterilization.

U.S. Pat. No. 4,744,951 to Cummings et al. discloses a two-chambered system which provides hydrogen peroxide in vapor form for use in sterilization processes. The sterilant is initially vaporized in one chamber and then applied to the object to be sanitized in another single sterilizing chamber, thereby producing a concentrated hydrogen peroxide vapor which is relatively more effective. The sterilization processes are designed for furnishing concentrated hydrogen peroxide vapor to interior surfaces of articles having a tortuous or a narrow path. However, the sterilization processes are ineffective at rapidly sterilizing lumened devices, since they depend on the diffusion of the hydrogen peroxide vapor into the lumen to effect sterilization.

U.S. Pat. No. 4,863,688 to Schmidt et al. discloses a sterilization system consisting of a liquid hydrogen peroxide vaporization chamber and an enclosure for sterilization. The enclosure additionally may hold containers wherein the hydrogen peroxide sterilant vapor does not contact the interior of the containers. This system is designed for controlling the exposure to the hydrogen peroxide vapor. The system is not designed for sterilizing a lumen device.

U.S. Pat. No. 4,943,414, entitled "Method for Vapor Sterilization of Articles Having Lumens," and issued to Jacobs et al., discloses a process in which a vessel containing a small amount of a vaporizable liquid sterilant solution is attached to a lumen, and the sterilant vaporizes and flows directly into the lumen of the article as the pressure is reduced during the sterilization cycle. This system has the advantage that the water and hydrogen peroxide vapor are pulled through the lumen by the pressure differential that exists, increasing the sterilization rate for lumens, but it has the disadvantage that the vessel needs to be attached to each lumen to be sterilized.

U.S. Pat. Nos. 4,937,046, 5,118,471 and 5,227,132 to Anderson et al. each disclose a sterilization system which uses ethylene oxide gas for sanitation purposes. The gas is initially in a small first enclosure and thereafter slowly permeates into a second enclosure where the objects to be sterilized are located. A medium is then introduced into the second enclosure to flush out the sterilizing gas into a third enclosure containing the second enclosure. An exhaust system then exhausts the sterilant gas and air from the third enclosure. These systems also have the disadvantage of relying on the diffusion of the sterilant vapor to effect sterilization and hence are not suitable for rapidly sterilizing lumened devices.

U.S. Pat. No. 5,122,344 to Schmoegner discloses a chemical sterilizer system for sterilizing items by vaporizing a liquid chemical sterilant in a sterilizing chamber. Pre-evacuation of the sterilizer chamber enhances the sterilizing activity. Sterilant is injected into the sterilizer chamber from a second prefilled shot chamber. This system also relies upon diffusion of sterilant vapor to effect sterilization and is also not suitable for rapidly sterilizing lumened devices.

U.S. Pat. No. 5,266,275 to Faddis discloses a sterilization system for disinfecting instruments. The sterilization system contains a primary sterilization chamber and a secondary safety chamber. The secondary safety chamber provides for sensing and venting to a destruction chamber any sterilization agent that is released from the primary sterilization chamber. This system, as in other systems, also relies upon diffusion of sterilant vapor to effect sterilization and is also not suitable for rapidly sterilizing lumened devices.

In U.S. Pat. Nos. 5,492,672 and 5,556,607 to Childers et al, there is disclosed a process and apparatus respectively for sterilizing narrow lumens. This process and apparatus uses a multicomponent sterilant vapor and requires successive alternating periods of flow of sterilant vapor and discontinuance of such flow. A complex apparatus is used to accomplish the method. Additionally, the process and apparatus of '672 and '607 require maintaining the pressure in the sterilization chamber at a predetermined subatmospheric pressure.

In U.S. Pat. No. 5,527,508 to Childers et al., a method of enhancing the penetration of low vapor pressure chemical vapor sterilants into the apertures and openings of complex objects is disclosed. The method repeatedly introduces air or an inert gas into the closed sterilization chamber in an amount effective to raise the pressure to a subatmospheric pressure to drive the diffused sterilant vapor further into the article to achieve sterilization. The '508, '672 and '607 Childers inventions are similar in that all three require repeated pulsations of sterilant vapor flow and maintenance of the sterilization chamber pressure at a predetermined subatmospheric pressure.

One disadvantage of the cleaning/sterilizing or cleaning/disinfecting systems of the prior art as discussed above is that, after the device is sterilized or disinfected and before it is dried, the device has to be rinsed with purified water to remove disinfectant or sterilant residues. A so-called bacteria filter is usually used to filter the water to remove particulates and bacteria. Typically, a two-stage filtering system is utilized, for example, a first stage has a 2–5 micron filter and a second stage has a 0.1–0.2 micron filter. However, virus can be smaller than 0.1 micron. This means the virus can penetrate the filtering system recontaminating the sterilized device in the final rinsing process. Another problem associated with the use of a bacteria filter is that bacteria can form biofilms in the filter which are difficult to sterilize and, thus, become a new potential source of contamination.

In consideration of the foregoing, no simple, safe, effective method of cleaning, sterilizing or disinfecting, drying devices with an integrated process and with the sterilizing (or disinfecting) and drying being conducted simultaneously exists in the prior art. Thus, there remains a need for a simple and effective process and apparatus for efficiently cleaning, sterilizing or disinfecting, and drying medical devices, especially those with long narrow lumens.

SUMMARY OF THE INVENTION

One aspect of the present invention provides a cleaning/sterilizing or cleaning/disinfecting process which incorporates cleaning, sterilizing (or disinfecting) and drying of a lumen or non-lumen medical device into an integrated process, i.e. the device is cleaned, sterilized and dried in situ in the same apparatus in a operation cycle. Especially, the sterilizing and drying are conducted simultaneously. In other words, after the device is sterilized, there is no need to further rinse the sterilized device like the prior art does. Thus, there is no need for a filtering system.

Another aspect of the present invention relates to an apparatus for cleaning, sterilizing, or disinfecting medical devices, especially devices with lumens. The apparatus comprises a container with an interface for separating the container into enclosures. The interface has an opening equipped with specially designed holder(s) for eliminating or reducing occlusion area Still another aspect of the present invention relates to a multi-compartment container. The container has a specially designed tray for accommodating a lumen device. The tray is placed across and sealed against an interface separating the container into enclosures.

The method of the present invention for cleaning/sterilizing or cleaning/disinfecting a device having a lumen with at least two open ends comprises the steps of: a) providing a container having at least one enclosure and at least one interface separating the enclosure from the container, the interface having at least one opening thereon, b) placing the device across the opening with one open end in the container and another open end in the enclosure, c) generating a flow of a cleaning solution through the lumen to clean the inner surface of the lumen, d) generating a flow of rinse solution through the lumen to rinse the inner surface of the lumen, e) treating the device with a chemical germicide, and f) adjusting the opening in any of steps c) to e) to reduce areas on outer surface of the device which are occluded from exposure to the cleaning solution, the rinse solution, or the chemical germicide by contacting with the opening, or to expose the areas to the cleaning solution, the rinse solution, or the chemical germicide. In the method, one or more steps can be repeated. In the method, along its passage, the opening has at least two independently controllable apertures for holding and sealing the device. In the method, the step of adjusting the opening comprises opening one of the two apertures while closing the other aperture so that the areas on the outer surface of the device occluded by the two apertures are alternately exposed to the cleaning solution, the rinse solution, or the chemical germicide in step c), d), or e), respectively. The method further comprises retaining a predetermined amount of the chemical germicide in the container and enclosure and vaporizing the retained chemical germicide to sterilize (or disinfect) and dry the device under vacuum during or after step e). In the method, the sterilizing or disinfecting can be conducted under a diffusion restricted environment, or by reducing pressure to a first predetermined pressure followed by further reducing the first pressure to a predetermined second pressure, or at controlled pump down rate. In the method, the sterility of said device can be maintained in the container and enclosure after the device is sterilized and dried. The method further comprises removably attaching the container to a vacuum system for applying vacuum to the container or enclosure and detaching the container after the device is sterilized (or disinfected) and dried. In the method, the flow through the lumen can be generated by applying a pressure higher than atmospheric pressure at one end of the lumen, or by applying vacuum to one end of the lumen device. In the method, the opening of the interface has separately controllable and moveable contact points, and the adjusting step comprises controlling the contact points so that a different portion of the contact points is made in contact with the device alternately. In the method, the opening forms a seal around the device selected from the group consisting of a gas-tight seal, a tight-fitting seal, or a loose-fitting seal. In the method, a non-lumen device also can be treated together with the lumen device.

An apparatus of the present invention for cleaning/sterilizing or cleaning/disinfecting a lumen device having at least two open ends comprises a container having a fluid port for flowing and draining a fluid in and out the container. At least one enclosure is coupled with the container for receiving part of the lumen device so that one end of the lumen device is located in the enclosure and the other end of the lumen device is located in the container. An interface separates the container and enclosure, and the interface has at least one opening. At least one openable and closable holder sealably is coupled to the opening. A source for creating a pressure difference between the two open ends to generate a flow through the lumen of the lumen device is provided. A cleaning mechanism adapted to clean the device in the container or enclosure is also provided. Preferably, the interface is removable. The holder can be a shutter. The holder can be equipped with expandable or compressible material on its contact surface with the device. In one embodiment, the holder has two plates forming a gap therebetween for passing the device, the surfaces of the plates facing the gap are equipped with expandable or compressible material. In another embodiment, two independently controllable holders are sealably arranged along the passage of the opening. Each one of the two holders comprises two plates forming a gap therebetween for passing the device, the surfaces of the plates facing the gap are equipped with expandable or compressible material. Preferably, each of the gaps defines an elongate cross section having a longitudinal axis as viewed from a direction perpendicular to the surface of the plates, the longitudinal axis of one gap forms an angle with that of the other gap, and the two holders are placed close enough to each other for the expandable material on one holder to be brought in contact with the other holder when the expandable material is expanded. The apparatus further comprises a vacuum system, the container comprises a gas-permeable and microorganism-impermeable barrier and is detachably coupled to the vacuum system. The gas-permeable and microorganism-impermeable barrier can be equipped with a valve for opening and closing gas communication between the container and the vacuum system or between the container and atmosphere through the barrier. The cleaning mechanism is selected from the group consisting of a stirrer, a liquid jet, an air jet, ultrasonics, or a bubble generator. The interface may comprise a first plate having a plurality of openings with elongate cross section, and at least two other plates forming a gap along a longitudinal direction, the plates are configured so that the longitudinal direction of the gap and the longitudinal direction of the elongate cross section of the opening form a substantially right angle. In another embodiment, the container has a first enclosure sharing with the container a first interface having a first opening and a second enclosure sharing with the first enclosure a second interface having a second opening, wherein the device is placed across the first and second interface through the first and second opening so that one open end of the device is located in the container and the other open end of the device is located in the second enclosure. In the apparatus of the present invention, the holder has multiple contact points on its inner surface for holding the device, and the contact points are separately controllable and moveable.

BRIEF DESCRIPTION OF THE DRAWINGS

FIG. 1a is a schematic diagram of a container used in a cleaning/sterilizing process of the present invention.

FIG. 3b is a schematic diagram of a shutter used in the interface of the container of FIG. 3a.

FIG. 3c is a schematic diagram of a iris valve used in the interface of the container of FIG. 3a.

FIGS. 3d, 3e, and 3f are schematic diagrams of two plates forming an opening in the interface of the container of FIG. 3a.

FIG. 3g is schematic diagram of an interface of the container of FIG. 3a.

FIG. 5a is a schematic diagram of a container having two holders in an interface.

FIG. 5b and 5c are schematic diagrams of two holders of the container shown in FIG. 5a holding a lumen device.

FIGS. 7b and 7c are cross-sectional views of the container of FIG. 7a at the location of the interface.

FIG. 8a is a top view of the container of FIG. 7a.

FIG. 8b is a top view of a portion of the interface of FIG. 7a.

FIG. 8c is a top view of the tray of FIG. 7a.

DETAILED DESCRIPTION OF THE PREFERRED EMBODIMENT

Figure 1C:
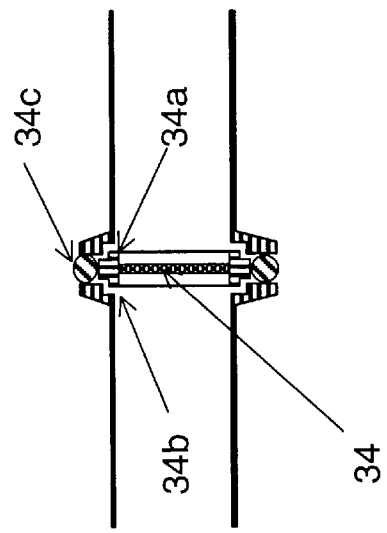
FIG. 1c is a schematic diagram of a gas-permeable but microorganism-impermeable barrier installed in a vacuum port of the container of FIG. 1.

The cleaning/sterilizing or cleaning/disinfecting process of the present invention can be carried out with various apparatus and incorporated with various sterilization methods, which are described below.

Method to Deliver a Predetermined Amount of Liquid Sterilant

This method can be incorporated into the cleaning/sterilizing or cleaning/disinfecting process of the present invention. In order to maximize the efficiency of a vapor sterilization process, it is important and desirable to drain excess sterilant solution and only keep a desired amount of the sterilant solution to vaporize after treating a device to be sterilized with the sterilant solution.

According to the present invention, a sterilization container or enclosure may have a surface with wells thereon which define a known volume. The well is positioned so that when a liquid sterilant is introduced onto the surface, a known volume of the liquid sterilant fills the well and when the liquid sterilant is drained from the surface, the known volume of liquid sterilant remains in the well so that a subsequent vapor sterilization process can be performed on the device with the known volume of liquid sterilant positioned within the surface. The surface preferably has at least one perforation for draining the liquid sterilant from the surface. The well formed in the surface can be curved, flat or angled. Thus, the well can be an inwardly extending hemispherical projection. The well can also be formed in the surface as an inwardly extending rectangular projection having rounded ends. The well formed in the surface can also be a rectangular box having side walls, defining an opening. Where perforations are provided, they can be disposed adjacent the well, and can be roughly spherical in shape. The upwardly extending projection can include a perforation thereon, which can be on top of the projection or on a side of the projection. The surface can be a sloped surface, a convex or concave surface or a V-shaped surface. The surface can be made of a variety of materials including stainless steels, aluminum, aluminum alloys, liquid crystal polymers, polyesters, polyolefins polymers or fluorinated polyolefins. If the surface is comprised of a composite material, the composite material can include a filler of high thermal conductivity. Examples of composite materials include a metal-filled polymer, a ceramic-filled polymer and a glass-filled polymer. Those materials are also suitable for the side walls and doors of the sterilization container.

A tray with wells with configurations similar to that described above can be provided with a container or enclosure. The tray can be secured to the container or removably placed in the container.

Method Based on Diffusion Restricted Environments

A method of vapor sterilization or disinfection under diffusion-restricted environments can also be used in corporation with the cleaning/sterilizing or cleaning/disinfecting process of the present invention. In this method, the devices (lumen or non-lumen) to be sterilized are pretreated with a sterilant solution, and then exposed to pressures less than the vapor pressure of sterilant. Both the exterior and interior surface areas of a lumen or non-lumen device can be effectively sterilized by taking advantage of the diffusion-restricted environments within lumens or within a container or enclosure.

As used herein, a "diffusion-restricted" area refers to any one or more of the following properties: (1) the ability of the area of an article placed within the sterilization system of the present invention to retain 0.17 mg/L or more hydrogen peroxide after one hour at 40° C. and 10 torr; (2) having the same or more diffusion restriction than provided by a single entry/exit port of 9 mm or less in internal diameter and 1 cm or greater in length; (3) having the same or more diffusion restriction than provided by a lumen 27 cm in length and having an internal diameter of 3 mm; (4) having the same or more diffusion restriction than provided by a lumen having a ratio of length to internal diameter greater than 50; (5) the ability of an article placed within the sterilization system of the present invention to retain 17% or more of the starting 1 mg/L hydrogen peroxide solution initially placed therein after one hour at 40° C. and 10 torr; or (6) being sufficiently diffusion-restricted to completely sterilize a stainless steel blade within a 2.2 cm by 60 cm glass tube having a rubber stopper with a 1 mm by 50 cm stainless steel exit tube therein at a vacuum of 10 torr for one hour at 40° C. in accordance with the present invention. It is acknowledged that characteristics (1) and (5) will vary depending on the initial concentration of hydrogen peroxide placed into the article; however, this can be readily determined by one having ordinary skill in the art.

This method includes the steps of contacting the exterior and interior of a device with a sterilant solution, and then exposing the device to a negative pressure or vacuum for a period of time sufficient to effect complete sterilization. For example, when 1 mg/L of hydrogen peroxide is used as sterilant, if the exposing step is conducted for 1 hour at 40° C. and 10 torr, the diffusion restricted area preferably retains 0.17 mg/L or more hydrogen peroxide, or retains 17% or more of the hydrogen peroxide placed therein after the exposing step. In certain preferred embodiments, the diffusion-restricted area has the same or more diffusion restriction than provided by a lumen 27 cm in length and an internal diameter of 3 mm, or has the same or more diffusion restriction than provided by a lumen having a ratio of length to internal diameter greater than 50. The contacting step can be performed by either a direct or an indirect contact procedure. Direct contacting includes methods such as injection, static soak, flow-through, condensation of a vapor, or aerosol spray, or mist spray. Any other methods involving physically contacting the devices to be sterilized with a sterilant would be considered direct contacting. Indirect contacting includes those methods in which sterilant is introduced into the chamber or container, but not directly on or on the devices to be sterilized. The exposing step is preferably performed for 60 minutes or less, and is preferably performed at a pressure less than the vapor pressure of the sterilant. Thus, the preferred pressure range under conditions of the present invention is between 0 and 100 torr. The exposing step can include the step of heating the device, such as by heating the container in which the exposing step occurs. The container can be heated to about 40° C. to about 55° C. Alternatively, the sterilant solution can be heated, such as to a temperature of about 40° C. to about 55° C. Optionally, the step of exposing the device to a plasma can be conducted during the step of exposing the device to negative pressure or vacuum. In one embodiment employing exposure to plasma, the method is performed within a first chamber and the plasma is generated in a second separate chamber. This embodiment further comprises the step of flowing the plasma into the first chamber. Advantageously, the contacting and/or exposing steps of the method can be repeated one or more times.

Method Based on Controlled Pump-Down Rate

The cleaning/sterilizing process of the present invention can also be carried out in cooperation with a controlled pump down method without relying on a diffusion-restricted environment.

Effective sterilization results similar to those created in diffusion-restricted environments can be created through controlling the evacuation rate of a chamber or container in which devices to be sterilized are placed. Thus, in one embodiment of the present invention, this controlled pump-down rate method comprises the steps of contacting the device with a liquid sterilant at a first pressure; draining excess liquid sterilant to retain a predetermined amount of the sterilant, and decreasing the pressure of the chamber to a second pressure below the vapor pressure of the liquid sterilant in which at least a portion of the decrease in pressure below about the vapor pressure of the liquid sterilant occurs at a pump down rate of less than 0.8 liters per second, calculated based on the time required to evacuate the chamber from atmospheric pressure to 20 torr when the chamber is empty and dry, i.e. when the chamber has neither devices to be sterilized nor a visible quantity of liquid within it. According to one aspect of this preferred embodiment, at least the decrease in pressure below about two times the vapor pressure of the liquid sterilant occurs at a pump down rate of less than 0.8 liters per second. According to another embodiment, the decrease in pressure below about four times the vapor pressure of the liquid sterilant occurs at a pump down rate of less than 0.8 liters per second. Preferably, the pump down rate is 0.6 liters per second or less; more preferably, 0.4 liters per second or less; and most preferably, 0.2 liters per second or less. Advantageously, the first pressure is atmospheric pressure. Preferably, the liquid sterilant is hydrogen peroxide. The hydrogen peroxide usually is a solution as used in the art, preferably it is a 3–60% solution. The device can be a lumen or non-lumen medical instrument.

The present invention can also incorporate a method for sterilizing a device comprising the steps of (a) contacting the device with liquid sterilant at a first pressure; (b) retaining a predetermined amount of the liquid sterilant in the container; (c) pumping down the container or chamber to a second pressure which is lower than the first pressure at a first rate; and (d) pumping down the container or chamber to a third pressure which is lower than the second pressure, wherein at least a portion of the pumping down to the third pressure is at a second rate which is slower than the first rate. The pump down rate either above and/or below the second pressure can be constant or variable. In certain embodiments, the pump down rate either above and/or below the second pressure is reduced in stepwise fashion. Preferably, the second pressure is greater than or equal to about the vapor pressure of the liquid sterilant; more preferably, the second pressure is greater than or equal to about two times the vapor pressure of the liquid sterilant; most preferably, the second pressure is greater than or equal to about four times the vapor pressure of the liquid sterilant. Advantageously, the pump down rate in step (d) is 0.8 liters/sec or less; more advantageously 0.6 liters/sec or less; even more advantageously 0.4 liters/sec or less; and most advantageously 0.2 liters/sec or less, calculated based on the time required to evacuate the chamber from atmospheric pressure to 20 torr under empty and dry conditions. Preferably, the liquid sterilant is hydrogen peroxide. In another embodiment, the device is a medical instrument having a lumen. Preferably, the pumping down of step (c) reduces the pressure to less than about three times, more preferably to less than about two times, the vapor pressure of the liquid sterilant.

Another suitable method includes contacting the device with liquid sterilant, retaining a predetermined amount of the liquid sterilant in the container, and reducing the pressure of the chamber while regulating the pump down rate so as to control the evaporation rate of sterilant in said chamber. In any of the methods described above, the contacting step may comprise application of liquid or condensed vapor. These methods described above may additionally comprise further evacuating the chamber to remove residual sterilant. Further, these methods described above may additionally comprise exposing the device to plasma to remove residual sterilant or enhance sterilization efficacy. The contacting step in these methods can be either by direct or indirect contacting. As stated herein, indirect contacting involves introducing sterilant into the chamber without directly contacting the device to be sterilized.

Two Step Pump-Down Method

A two step pump down sterilization method can also be used in cooperation with the cleaning/sterilizing process of the present invention. This method comprises the steps of contacting a device with liquid sterilant; draining excess liquid sterilant to retain a predetermined amount of the sterilant; bringing the pressure of the chamber to a first pressure range at which the liquid sterilant is vaporized from non-diffusion restricted area of the device to sterilize the non-diffusion restricted area; bringing the pressure of the chamber to a second pressure range at which the liquid sterilant is vaporized from diffusion restricted area of the device to sterilize the diffusion restricted area, wherein the minimum pressure in the second pressure range is lower than the maximum pressure in the first pressure range.

Preferably, the first pressure range is from 20 to 760 torr; more preferably, the first pressure range is 20 to 80 torr; most preferably, the first pressure range is 40–50 torr. Advantageously, the second pressure range is 1–30 torr; more advantageously, the second pressure range is 5–10 torr. In one preferred embodiment, the device includes a diffusion-restricted environment. Preferably, the device is a medical instrument with a lumen. Advantageously, the sterilant is hydrogen peroxide. According to another aspect of this preferred embodiment, the chamber is at a set temperature and wherein the first pressure is preferably lower than the vapor pressure of the sterilant at the set temperature. Preferably, the pressure of the chamber is maintained constant at the first pressure for a time period sufficient to sterilize the non-diffusion restricted area. Advantageously, the pressure of the chamber is maintained constant at the second pressure for a time period sufficient to sterilize the diffusion restricted area. The pressure of the chamber may be permitted to increase after reaching the first or second pressure range as a result of vaporization of the sterilant within said chamber. Alternatively, the pressure of the chamber is permitted to decrease after reaching the first or second pressure through pumping of said chamber at a rate slower than used to decrease the pressure between said first and second pressure ranges. Preferably, the contacting step is with liquid, condensed vapor, or mist. The method can also include the steps of bringing the pressure to a third pressure lower than the second pressure to remove residual sterilant and/or exposing the device to plasma to remove residual sterilant or enhance sterilization efficacy.

Method Involving Direct Flow Through a Lumen of the Device to Be Sterilized

A method of directly flowing fluid through a lumen of a medical device to be treated can be incorporated with the cleaning/sterilizing or cleaning/disinfecting process of the present invention. An apparatus can be used to efficiently clean and sterilize devices with long narrow lumens by flowing a fluid such as a cleaning solution or a sterilant, either in liquid phase or in vapor phase, or a plasma gas directly through the lumens of lumen devices to be sterilized.

The flow of a germicide (solution or vapor), or any cleaning solution through a lumen of a medical device is driven by a pressure drop between two open ends of the lumen. The pressure drop can be generated by applying either a vacuum or a high pressure at one end. By generating a forced flow through a pressure differential other than relying on diffusion, the sterilization rate is significantly increased and less time is needed for a sterilization cycle.

It is clear that the two ends of the lumen need to be exposed to a pressure differential. This is achieved in the present invention by placing a sealable interface between two chambers, two enclosures, or a container and an enclosure to separate them from each other. Preferably, an opening is provided in the interface and the lumen device to be sterilized is placed through the opening so that the lumen serves as a flow path between the two chambers or between the container and the enclosure.

The opening can be constructed in several ways. One way to achieve this is with a camera shutter approach employing an iris diaphragm, such as a precision iris diaphragm from Edmund Scientific. An optional spring can be used to secure the closure of the shutter. Also commercially available is Syntron Iris Flow Control Valve manufactured by FMC Corporation. This Iris Valve has a sleeve made of Teflon or other synthetic material defining an aperture. By rotating two ends of the sleeve relative to each other, the aperture can be reduced or increased. Iris diaphragm valves from Kemutec Inc. are also commercially available which can be automatically controlled. Another example is the AirGripper and AirPicker manufactured by Firesone Industrial Products Company. Another way to construct an openable and closeable opening is to employ two plates. Two edges of the two plates form a gap which can be adjusted by moving the two plates relative to each other. One or more lumen devices are placed through the gap formed between the two plates and the two plates are moved together to form a seal around the lumen devices. The edges of the two plates forming the gap can be equipped with compressible material or expandable material. When expandable material is used, a fluid source can be provided to expand the expandable material. Optionally, a porous material like a sponge or air permeable material may be utilized on the edges. In this case some sterilant can diffuse through the porous material to the outer surface of the lumen device occluded by the closed opening. However, most the sterilant flows through the lumen device. Another usable interface is a hole or a slot, the hole or slot is equipped with gas or liquid inflatable material so that by inflating the inflatable material on the hole or the slot the opening is reduced and the lumen device is held and sealed. Still another option is to place a compressible material on top of an expandable or inflatable material so as to facilitate the sealing around the lumen device.

The closing and opening movement of the opening can be controlled mechanically or electronically with any conventional mechanism. The degree of opening is adjustable. Thus, it can be sealed to a different degree between the opening and the lumen device depending on the desired purpose. For example, the opening can form a gas-tight seal, a tight-fitting seal, or a loose-fitting seal around the lumen device. As used herein, a gas-tight seal refers to a seal that substantially stops liquid and gas flow through the contact area between the opening and the lumen device surface. When a gas-tight seal is employed, preferably the device to be sterilized is first pre-cleaned so that the occluded area by the seal is cleaned before the gas-tight seal is formed. A loose-fitting seal allows both liquid and gas to flow through the gap between the opening and the lumen device surface, and in the meantime is able to maintain a pressure drop across the interface enough to generate a flow through the lumen. A tight-fitting seal allows gas and liquid to penetrate to the contact area between the opening and the lumen device surface by diffusion. For example, a tight-fitting seal can be formed with porous material or textures provided on the contact surface of the opening. Thus, for gas-tight seal the device is held tightly by the closed opening. In the tight-fitting seal, the closed opening also holds the device in position. In the case of a loose-fitting seal, the device can move relative to the opening, but is not flashed away.

The interface can be made openable, closeable, and removable, and may have more than one opening. In order to promote sterilization efficiency, all the sterilization apparatus of the present invention can be further equipped with a heater and/or a plasma.

Specially Designed Containers

As used herein, the terms "container" and "enclosure" are exchangeable. The present invention provides a container specially designed to eliminate or minimize occlusion area which usually corresponds to the contact area between a lumen device surface and a closed opening of an interface holding the device. The occlusion area is hard to reach by either liquid or vapor because of the close contact between two surfaces. Thus, the cleaning and sterilizing of an occlusion area is adversely affected by such contact. Several approaches have been taken in the present invention to deal with this occlusion problem.

One approach is to reduce the contact area by using porous material, textures, sharp projections, or sharp edges on the contact surface of the opening of the interface, or an adaptor or a connector. In this way, cleaning and sterilizing fluid can either flow or diffuse to most part of the contact surface of the device which is held by the closed opening fairly tightly and, in the meantime, the contact area between the opening and the device surface will impose a resistance to fluid flow high enough to allow a pressure difference to exist between two sides of the interface. Thus, a flow through the lumen of the device can be generated and maintained if desired. Another advantage of this approach is that the contract area generated through the above means can be controlled to provide a diffusion restricted environment at the contact area, which will increase the efficiency of the sterilization process.

Another approach is to use multiple holders in the opening. For example, two holders can be secured to the opening along its passage. Preferably, each of the holders is independently controllable and sealable. During a cleaning or sterilizing process, the two holders are alternately opened and closed, i.e. one is open while the other is close. In this way, a good seal between the two sides of the interface can be maintained and the device can be held tightly during a sterilization process. Meanwhile, the contact areas on the device surface caused by the two holders are exposed to cleaning or sterilizing fluid alternately.

Still another approach is the combination of the above two approaches. In this approach, the contact surface of the interface, or the opening, or the holder has multiple contact points. The contact points can be projections, teeth, blades, sharp edges, or any other suitable form and shape. These contact points can be controlled separately so that a portion of the contact points is made in contact with the device to be sterilized while the others are not. By alternately changing the position of the contact points, all the occlusion areas will be exposed to the sterilant. An example of such a multiple contact point structure is a shutter with multiple blades. Those blades can be separately controlled for opening and closing.

The present invention also provides a container with a specially designed tray. It is often desirable to place the device to be sterilized on a tray so that after the device is cleaned and sterilized, it can be transported on the tray without being touched. This reduces the chance of contamination through touching the device. In the apparatus of the present invention, a tray is placed across an openable and closeable interface between a container and an enclosure or between two compartments or enclosures, a lumen device is placed on the tray also across the interface. When the interface is in a closed condition, a seal is formed between the opening of the interface and the tray and the lumen device.

Various apparatus of the present invention which can be used to carry out the cleaning/sterilizing or cleaning/disinfecting process of the present invention is described in more detail by reference to the drawings. In the following figures like numbers refer to like parts throughout.

Figure 1B:
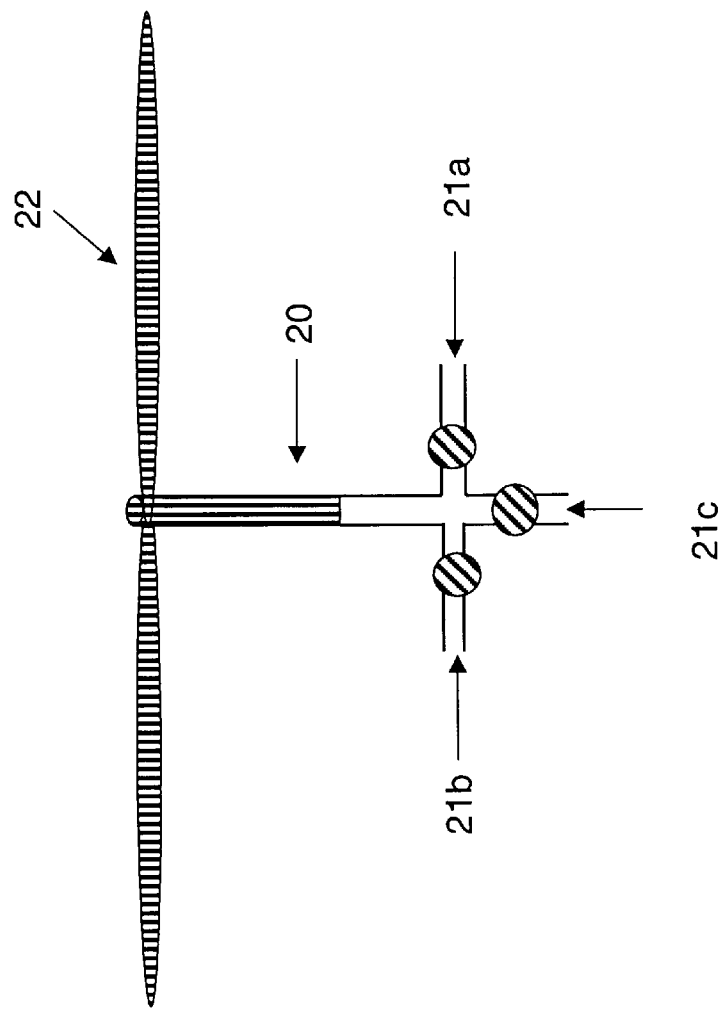
FIG. 1b is a schematic diagram of a stirrer with fluid inlets used in the container of FIG. 1.

FIG. 1a shows a container 2 used in a cleaning/sterilizing process of the present invention. Container 2 has a sloped bottom wall 4 leading to a fluid source 7. A fluid port 6 is provided at the lowest point of sloped bottom wall 4. Apparently, sloped bottom wall 4 can be configured differently and the lowest point can be located in any location within the sloped bottom wall 4. For example, instead located in the position as shown in FIG. 1a, the lowest point, thus the fluid port 6, can be located at one end or a corner of the sloped bottom wall 4. A valve 8 is provided at fluid port 6 to control fluid flow in and out container 2. Below sloped bottom wall 4 is a flat lower bottom 14. The lower surface of the sloped bottom wall 4 is equipped with a number of transducer 16 for providing ultrasonic cleaning. A number of wells 18 are provided on a plate 17 located above the upper surface of the sloped bottom wall 4 and below rotating arm 22. Plate 17 can be of any appropriate shape and made rotatable, so that unwanted liquid retained in wells 18 can be removed by rotating plate 17. Well 18 can have different shapes and is capable of retaining a predetermined amount of sterilant as described earlier. Plate 17 can be removably placed on the upper surface of the sloped bottom wall 4 or secured to the upper surface in a horizontal orientation. One or more stirrer 20 is installed either on sloped bottom wall 4 or on an upper wall 24 or on both. Rotating arm 22 of the stirrer 20 can be made hollow or contains channels connecting to an outside fluid source through the body of the stirrer 20. As shown in FIG. 1b, stirrer 20 can be connected to a water source 21a, an air source 21b, and a drain 21c, each of them is controlled by a valve. Water jet or air jet 26 can be provided through the channels of rotating arm 22. Container 2 can also be made of jacket walls with holes thereon so that the water or air jet can be provided through those holes opened on the jacket walls. Container 2 also has a lower grid 28a and an upper grid 28b. Preferably, grid 28b and 28a has a flat shape and horizontally placed inside container 2 at an upper and a lower position, respectively. A space defined by lower grid 28a, upper grid 28b and side walls of container 2 is used to accommodate a device to be treated. A tray 30 can be placed in the space and the device is placed in the tray 30 for cleaning and sterilizing. Stirrer 20 is located either in the space defined by upper wall 24, upper grid 28b and side walls of container 2, or in the space defined by sloped bottom wall 4, lower grid 28a and side walls of container 2, or in both. Container 2 further contains a vacuum port 32 located at the upper portion of container 2. Preferably, vacuum port 32 is located on the upper wall 24 of container 2 to avoid liquid in container 2 from entering vacuum port 32. A gas-permeable but microorganism-impermeable barrier 34 is secured to the vacuum port 32. Any conventional method can be used to seal barrier 34 into vacuum port 32 such as shown in FIG. 1c. In the connection shown in FIG. 1c, barrier 34 is placed in a barrier holder 34a. The barrier holder 34a is placed into a seat 34b formed between two end of two tubes. An O-ring 34c is provided around holder 34a. Thus, by clamping the two ends of the two tubes toward each other barrier 34 is secured and sealed. A valve 36 is provided at vacuum port 32. A vacuum pump 38 is connected to vacuum port 32 through valve 36. A detachable connector can be provided between valve 36 and vacuum pump 38.

Figure 1D:
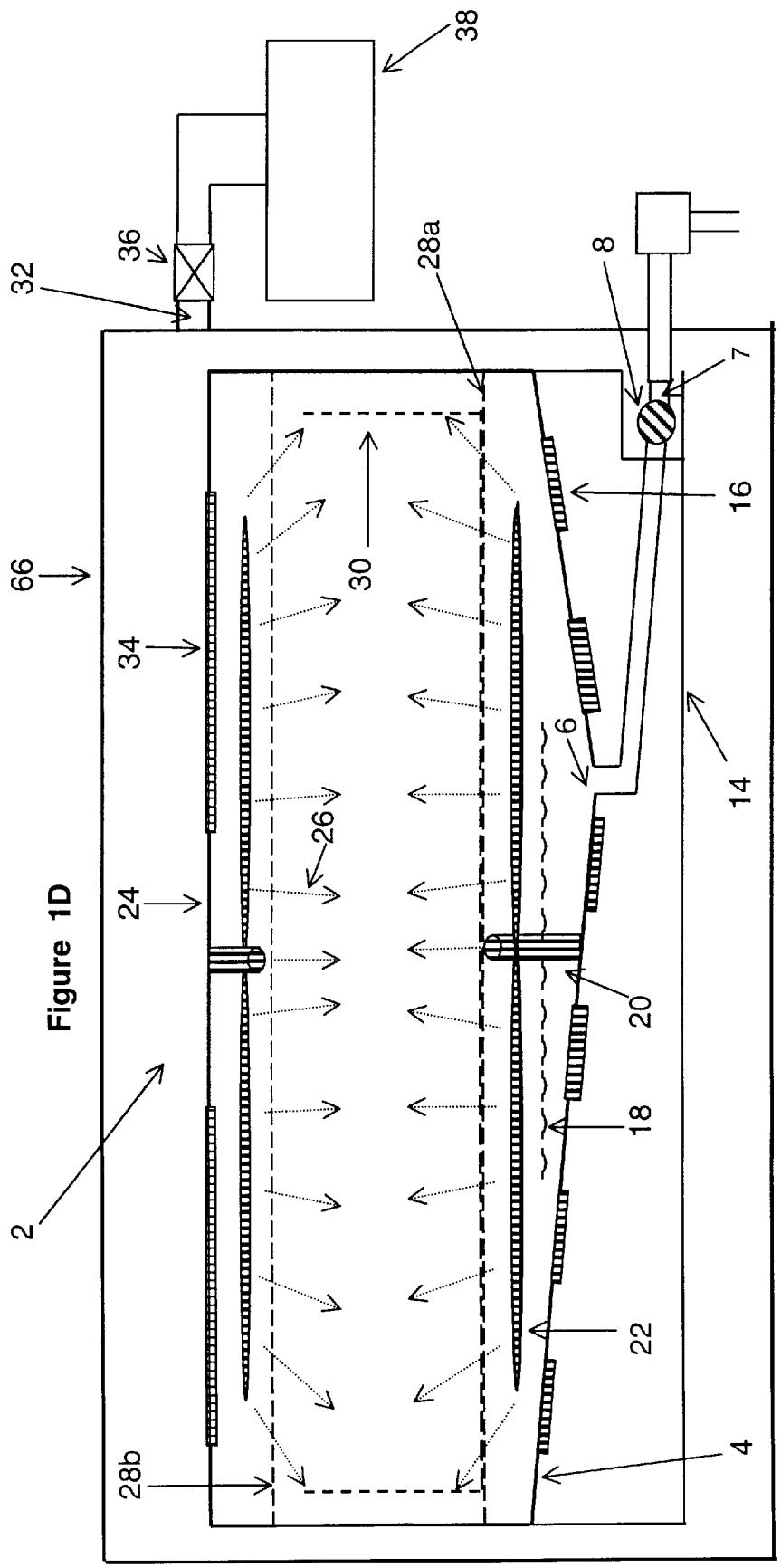
FIG. 1d is a schematic diagram of a container placed in a vacuum chamber used in a cleaning/sterilizing process of the present invention.

Container 2 of FIG. 1a can be placed into a vacuum chamber with slight modification. As shown in FIG. 1d, the same container 2 is used except that barrier 34 provided on upper wall 24 is not connected directly to the vacuum port 32 which is provided on the wall of a vacuum chamber 66.

Figure 1E:
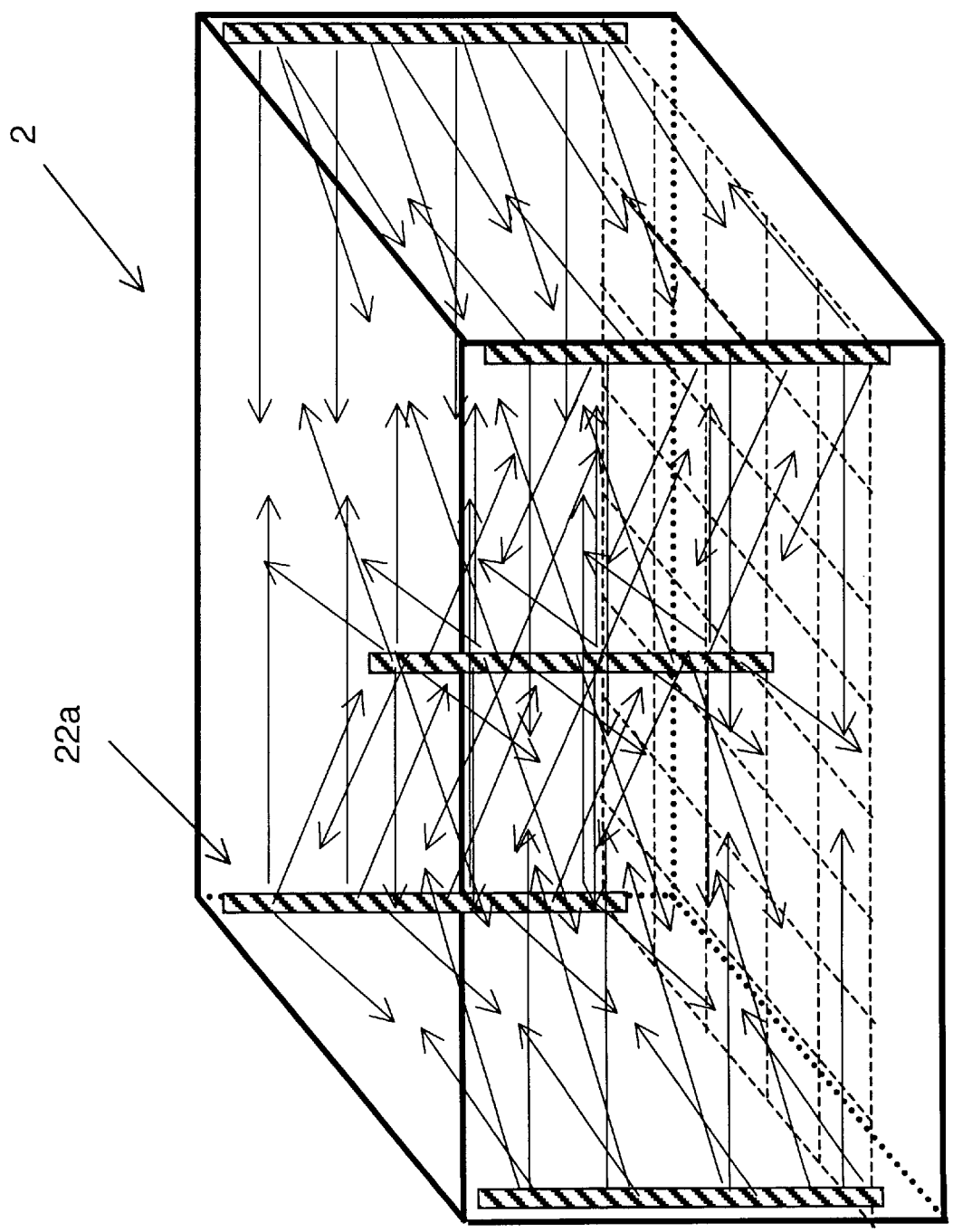
FIG. 1e is a schematic diagram of a container with fluid jet tubes.

FIG. 1e shows another way of providing a fluid jet in container 2. Instead of stirrers, several tubes 22a with small holes thereon are secured vertically in container 2 to provide a fluid jet such as a water jet or an air jet Tube 22a can be positioned to provide an uniform spray, the orientation and shape of tube 22a can be determined according specific purposes. The rest parts can be the same as the container of FIG. 1a.

When using the above described container in the cleaning/sterilizing process of the present invention, one first places a device into the container 2. The device can be either placed on the lower grid 28a or placed in tray 30. Two grids 28a and 28b set the boundaries for the devices in the container and keep the device from being damaged by stirrer 20. The upper grid 28b is the fluid fill line to ensure all the devices are immersed in the fluid. Usually the device is first pre-cleaned in container 2 by a water jet to remove majority of soils, large particles, and other contaminates. During the pre-cleaning, the drain is usually kept open to remove the dirty water containing those particles and contaminates. Then the device is cleaned. In this step a cleaning solution is filled into container 2 through a liquid pump. The cleaning solution can be any conventional cleaning solution with enzyme and detergent solution preferred. During the cleaning step, stirrers, water jet, ultrasonics, or other suitable mechanism can be used to facilitate the cleaning process. When the cleaning is complete, the cleaning solution is drained through fluid port 6. A rinse solution is then introduced into container 2 through fluid port 6. The rinse solution can be water, alcohols, or other rinse liquid. The rinsing can be facilitated by stirrers, water jet, air bubbles, or other suitable mechanism. These steps can be repeated if desirable. After the rinsing step, air can be introduced through stirrer 20 to blow water off the device. Then a liquid sterilant is introduced into container 2 from the same fluid port, and the device is treated with the liquid sterilant for a desired time. Preferably, the liquid sterilant is a hydrogen peroxide solution or a peracetic acid solution. The main purpose of this step is to treat the device with the liquid sterilant and to provide right amount of the liquid sterilant. The sterilization is achieved mainly in next step. If necessary, excess of the liquid sterilant can be drained from container 2, and a predetermined amount of the liquid sterilant will be retained by the wells 18. This amount of liquid sterilant is determined based on the size of the load, the container, and the vacuum chamber. At this point, vacuum pump 38 is turned on and vacuum is applied to container 2 through vacuum port 32. In this step, the diffusion restricted environment method, the controlled pump down rate method, the two step pump down method discussed previously can be employed to achieve good sterilization results. When the sterilization is finished, container 2 is detached from the vacuum system, the device can be kept in container 2 and stored for future use. The sterility of the sterilized device is maintained in container 2 because container 2 is sealed except for the gas-permeable but microorganism-impermeable barrier 34. In one embodiment, valve 36 is closed when the pressure in container 2 is lower than atmospheric pressure and container 2 including the sterilized device is stored for use. This procedure provides a further means to check if the sterility of the device is well maintained in the container. If the container 2 is still under a pressure below the atmosphere before next use of the device, that means no air leaking into container 2 and, thus, no microorganism can enter container 2 during the storage. Any one of the above steps can be repeated if desirable. The sterilizing step can also be replaced with a disinfecting step by using a proper germicide.

Figure 2:
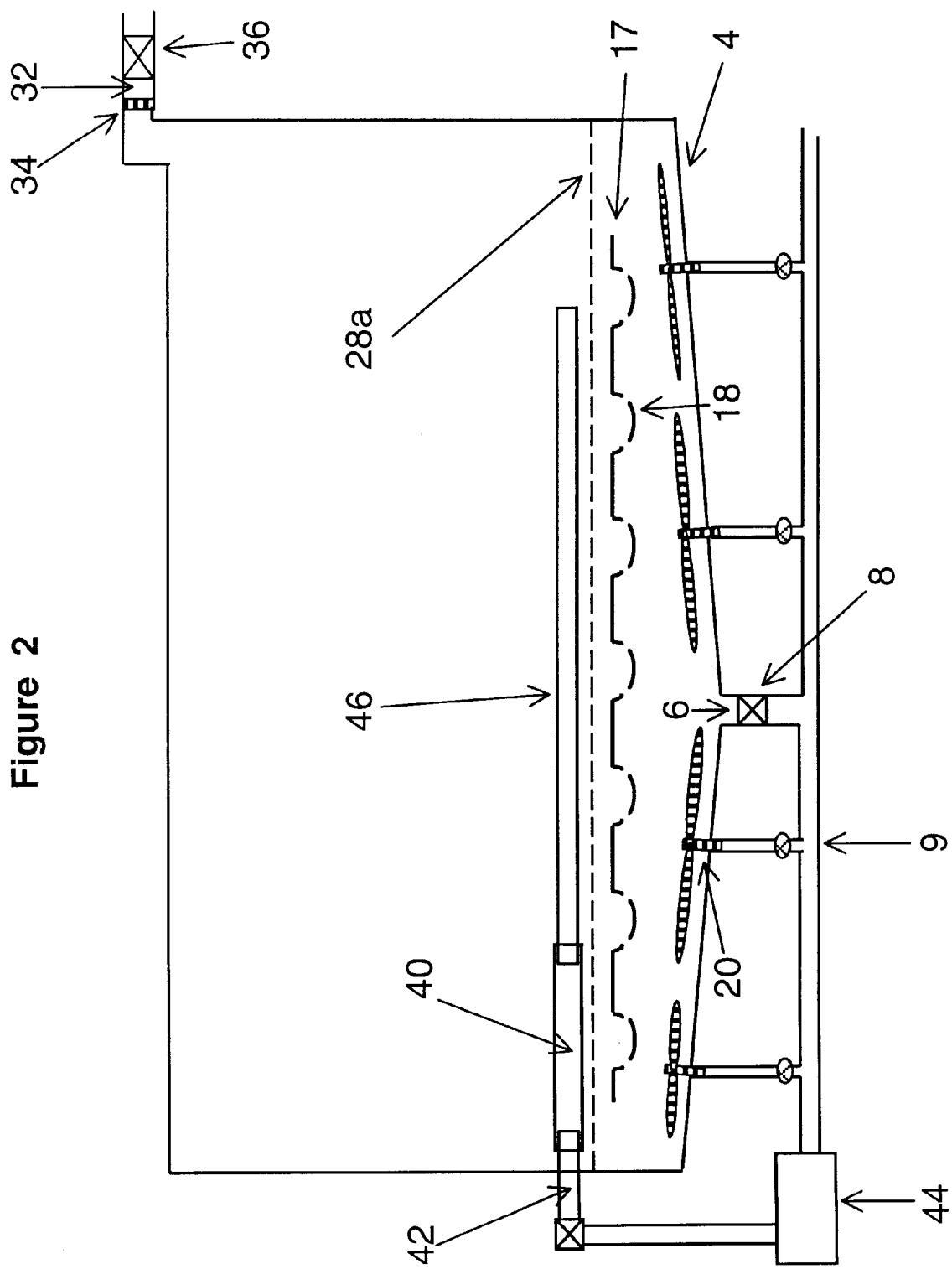
FIG. 2 is a schematic diagram of a container with an adaptor used in the cleaning/sterilizing process of the present invention.

FIG. 2 shows a container having adapters for connecting lumen devices. Similar to the container of FIG. 1a, container 2 shown in FIG. 2 has a sloped bottom wall 4 with a first fluid port 6 at the lowest point of the sloped bottom wall 4. Several stirrers are installed on the sloped bottom wall 4. A flat sheet metal grid 28a is horizontally located at the lower portion of container 2. Grid 28a, sloped bottom wall 4, and side walls of container 2 define a space accommodating stirrer 20 and wells 18 on plate 17. An adapter 40 is connected to a second fluid port 42 at one end and the other end for receiving a lumen device 46. A gas-tight seal, tight-fitting, or loose-fitting between adapter 40 and lumen device 46 can be formed. Adapter 40 can be any suitable conventional adapters used in the art. Preferably, the second fluid port 42 is located above grid 28a. Second fluid port 42 is also connected to a source 44 for generating a pressure difference between the two ends of a lumen device 46 which is connected with the second fluid port 42 through adapter 40. Source 44 can be a liquid pump for generating negative pressure, or a positive pressure. Lumen device 46 is placed on top of the grid 28a. Like the container shown in FIG. 1a, container 2 of FIG. 2 also has a vacuum port 32 with a gas-permeable but microorganism-impermeable barrier 34 and a valve 36. The barrier covers the vacuum port 32 and blocks passage for microorganism, valve 36 controls the opening and closing of the vacuum port 32. As shown, fluid port 6 and stirrers 20 are also connected with a tube 9 for draining fluid from container 2 or supplying fluid jet to stirrer 20. One end of tube 9 leads to a waste fluid collector, the other end is connected to pump 44.

Figure 3A:
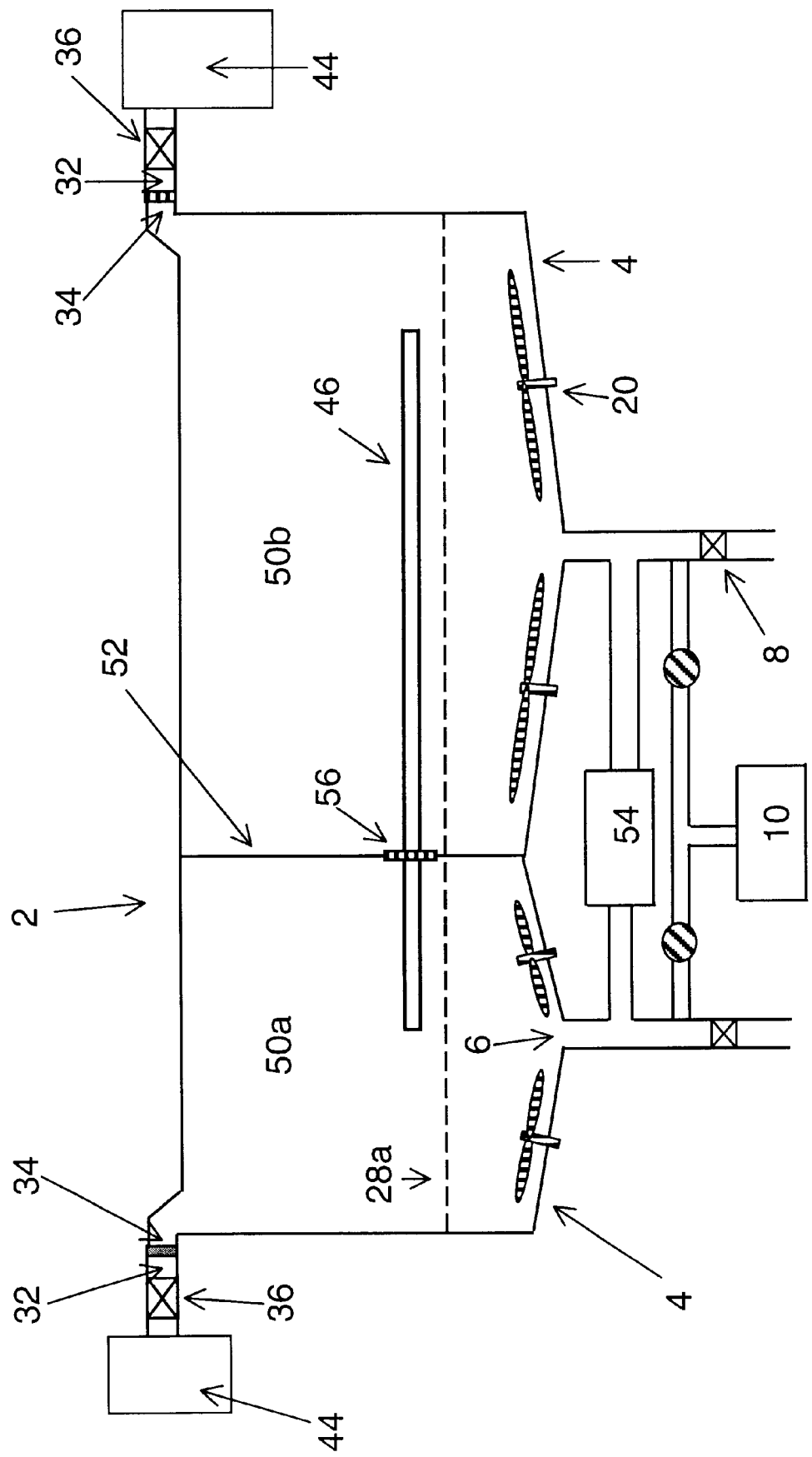
FIG. 3a is a schematic diagram of a container with an interface used in the cleaning/sterilizing process of the present invention.

FIG. 3a shows a container 2 separated into a first enclosure 50a and a second enclosure 50b by an interface 52. As shown both enclosure 50a and 50b have a sloped bottom wall 4 with stirrer 20 secured thereon, a flat sheet grid 28a horizontally positioned at lower portion of enclosure 50a and 50b, and a fluid port 6, respectively. A pump 54 is provided between the two fluid ports 6. A vacuum port 32 is provided at the upper portion of enclosure 50a and 50b. A gas-permeable but microorganism-impermeable barrier 34 is connected to the vacuum port 32 to stop microorganism from entering enclosure 50a and 50b through vacuum port 32. Vacuum port 32 is also equipped with a valve 36 and a source 44 for generating pressure difference and providing vacuum. Preferably, source 44 is a vacuum pump for providing negative pressure or compressed air for providing positive pressure. Interface 52 has a controllable opening 56 (also referred as holder). Lumen device 46 is placed across opening 56 partly in enclosure 50a and partly in enclosure 50b. Opening 56 can be configured differently. For example, opening 56 can be made of a shutter 58 such as an iris diaphragm as shown in FIG. 3b, and the opening and closing of opening 56 can be controlled manually or automatically. In one embodiment, the blades of shutter 58 (eight blades are shown in FIG. 3b), can be divided into two groups. For example, each group contains four blades not next to each other. These two groups of blades are controlled separately by a controller so that while one group is in the close position holding the device to be sterilized the other group is in open position allowing the sterilant to sterilize the area occluded by the blades when the blades are in closed position. Another example of shutter 58 is the Syntron Iris Flow Control Valve (by FMC Corporation) or the Iris diaphragm valves (Kemutec Inc.) as shown in FIG. 3c. Briefly, Iris valve 58a has a cylindrical sleeve 90 with two retaining rings 92 located at two ends of the cylindrical sleeve 90. Sleeve 90 is made of Teflon or other suitable plastic or rubber material. When in use, a lumen device is inserted through an aperture 94 of cylindrical sleeve 90. A first retaining ring 92 is secured and sealed to opening 56, a second retaining ring 92 is free to rotate and coupled to interface 52 through a conventional mechanical mechanism (not shown) so that the turning of the second retaining ring 92 can be controlled mechanically or electronically from outside container 2. By rotating the retaining rings 92 relative to each other, the diameter of aperture 94 of the cylindrical sleeve 90 can be increased or reduced, or totally shut off. If desirable, more than one shutter can be provided in the interface 52.

Opening 56 also can be a slot or a gap defined by two plates 59 as shown in FIGS. 3d and 3e. The contact edges or surfaces of plate 59, which form the slot and hold the lumen device 46, are equipped with a layer of expandable material 60 such as silicon, or a layer of compressible material 62. The closing, and thus seal around lumen device 46, of the slot can be done either by moving plate 59 or expanding expandable material 60. With a two-plate opening 56, more than one lumen device can be placed across the opening 56. When expandable or inflatable material is used on plate 59, an expansion fluid source can be provided to plate 59 to expand the expandable material 60. In one embodiment, a layer of compressible material 62 is provided on top of the layer of expandable material 60 as shown in FIG. 3f. In another embodiment, the opening 56 is formed by an upper plate 59a and a lower plate 59b as shown in FIG. 3g. The lower plate 59b has a rectangular shape with a bottom edge and two side edges being secured and sealed to the bottom wall and two side walls of container 2, respectively. The upper plate 59a also has a rectangular shape and its upper portion is movably inserted into a housing 53a. Housing 53a forms the upper portion of interface 52. A portion of housing 53a extends along two side walls of container 2 to the upper edge (or contact surface) of lower plate 59b, forming two rails 53b for receiving the two side edges of upper plate 59a and guiding the movement of the upper plate 59a. There provided a seal between the upper plate 59a and the housing 53a and rail 53b. For example, an O-ring can be used in housing 53a and rail 53b to seal the upper plate 59a. The upper edge of the lower plate 59b and the lower edge of the upper plate 59a are provided with a layer of compressible or expandable material. The movement of the upper plate 59a can be controlled by any suitable conventional method, mechanically or electrically, form the outside of container 2. Many different configurations and structures can be adopted for the opening 56. For example, the contact surface of opening 56 can be made of an uneven surface so that, when opening 56 is closed around a lumen device, the uneven surface will provide passage to allow both liquid and gas to pass therethrough while holding the lumen device. Thus, the occlusion area on the lumen device surface can be significantly reduced. The uneven surface may have textures, projections, sharp edges, or sharp points thereon.

In another embodiment, opening 56 is an aperture equipped with a layer of porous material or with a layer of expandable material and a layer of porous material on top of the expandable material. Opening 56 also can be made of an aperture of suitable shape, such as cylindrical, lined with porous material. A shutter is secured to the aperture providing a steady holding of the lumen device 46 with minimal contact area or occlusion area.

Figure 4:
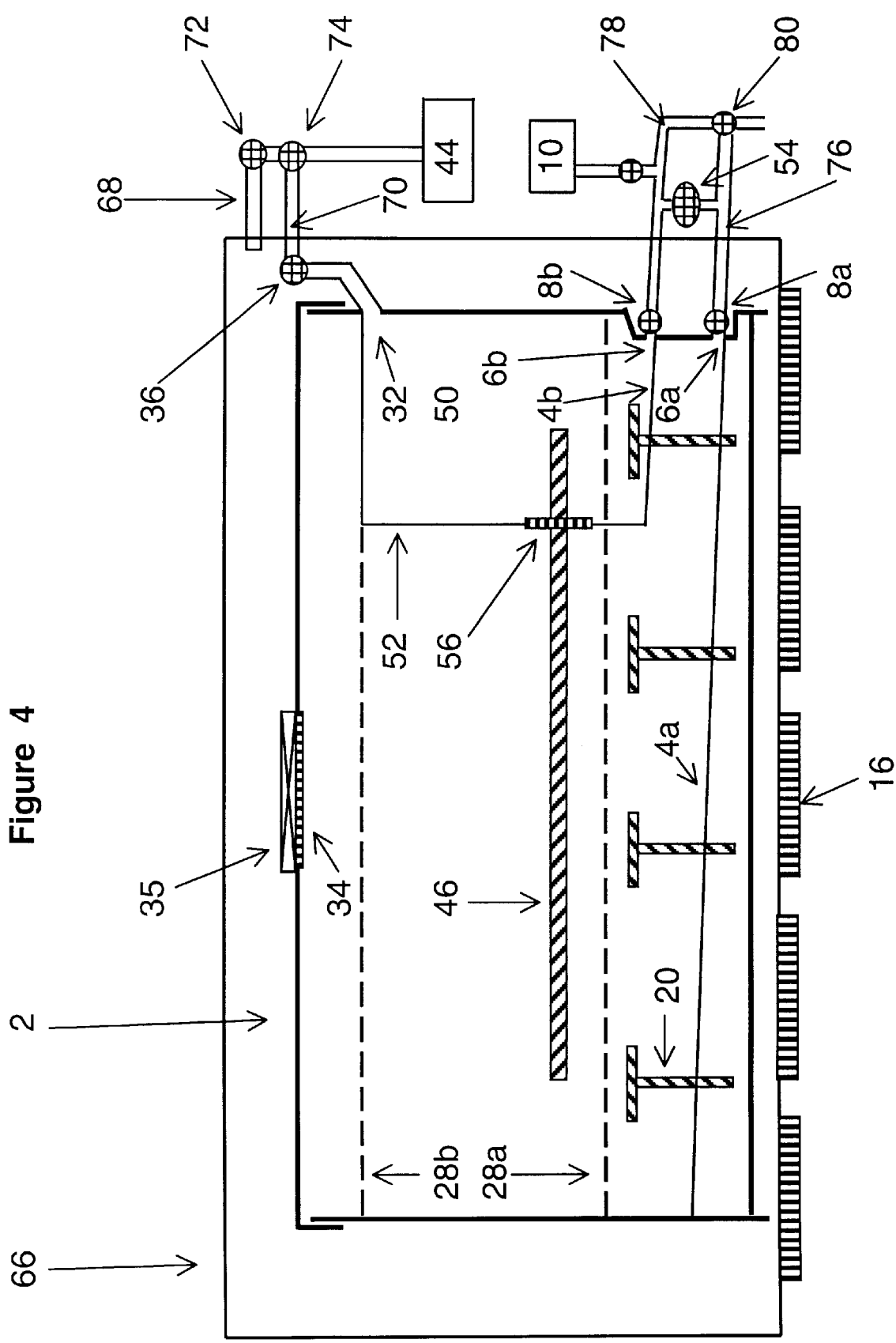
FIG. 4 is a schematic diagram of a container placed in a vacuum chamber used in the process of the present invention.

FIG. 4 shows a container 2 with an enclose 50 separated by an interface 52. In this embodiment, the container 2 with the enclosure 50 is placed inside and coupled to vacuum chamber 66. Vacuum chamber 66 has a first vacuum port 68 which is in gas communication with container 2 through a gas-permeable but microorganism-impermeable membrane 34 installed on the upper wall of container 2, and which is preferably located at the upper portion of a side wall of vacuum chamber 66. A valve 35 is provided above membrane 34 to control the opening and closing of gas communication of container 2 with outside through membrane 34. Vacuum chamber 66 also has a second vacuum port 70 connecting to a vacuum port 32 of the enclosure 50 through a valve 36. Preferably, the second vacuum port 70 also located at the upper portion of the side wall of the vacuum chamber and near the first vacuum port 68. Valve 36 is preferably located outside the enclosure 50 and inside the vacuum chamber 66. A detachable connector (not shown) is preferably provided between valve 36 and second vacuum port 70 for attaching valve 36 to and detaching valve 36 from the second vacuum port 70. The first and second vacuum ports 68 and 70 are connected to each other outside the vacuum chamber 66. A valve 72 is provided at first vacuum port 68 to control flow through the first vacuum port 68. A valve 74 can also be provided at the common inlet of the first and second vacuum ports 68 and 70. A source 44 for generating pressure difference between the two ends of the lumen device 46 is provided at the common inlet of first and second vacuum ports 68 and 70. Preferably, source 44 is a vacuum pump for generating a negative pressure or compressed air for generating a positive pressure. Vacuum chamber 66 also has a first fluid port 76 connecting to a fluid port 6a of the container 2 through a valve 8a, and a second fluid port 78 connecting to a fluid port 6b of the enclosure 50 through a valve 8b. The first and second fluid ports 76 and 78 are located at the lower portion of a side wall of the vacuum chamber 66 and close to each other. The fluid port 6a is located at the lowest point of a sloped bottom wall 4a of the container 2. In this embodiment, the fluid port 6a is located at one lower corner of the container 2. The fluid port 6b is located at the lowest point of a sloped bottom wall 4b of the enclosure 50. In this embodiment, the fluid port 6b is located at one lower corner of the enclosure 50. A detachable connector can be provided for connecting valve 8a and 8b to first and second fluid port 76 and 78, respectively. Outside the vacuum chamber 66, first and second fluid ports 76 and 78 are connected to each other forming a common fluid inlet which is provided with a valve 80. A liquid pump 54 is also provided between the first and second fluid ports 76 and 78 to circulate a fluid between the container 2 and the enclosure 50. The container 2 has a lower grid 28a and an upper grid 28b. Preferably, the lower grid 28a and the upper grid 28b are a flat metal sheet and horizontally positioned at the lower and the upper portion of the container 2, respectively. Stirrers 20 are located below the lower grid 28a. Interface 52 has an opening (or holder) 56 for holding a lumen device 46. The opening 56 can be configured in many different ways such as those described with FIGS. 3b–3f. On the bottom wall of vacuum chamber 66, a plurality of transducer 16 is provided to generate ultrasonics. Accordingly, the space between outer surface of the bottom of container 2 and the inner surface of the bottom wall of vacuum chamber 66 is filled with water or other suitable liquids providing a medium for the ultrasonics.

In using the apparatus with containers and enclosures separated by an interface in the cleaning/sterilizing or cleaning/disinfecting process of the present invention, a lumen device is placed into the container 2 and the enclosure 50 across the interface 52. The opening 56 of the interface 52 is then closed manually or automatically. Thus, opening 56 forms a seal around the lumen device. The extent of the sealing can be controlled through different degree of tightening of the opening 56 around the lumen device 46 for different purposes. As defined previously, three types of seal can be made between the opening 56 and the lumen device 46, gas-tight seal, loose-fitting seal and tight-fitting seal. If maximum pressure is intended a gas-tight seal should be used in this case the container 2 is substantially totally sealed from the enclosure 50, neither gas nor liquid can flow through the space between the opening 56 and the lumen device 46. Under many situations such a gas-tight seal is not necessary. In this case, a tight-fitting seal can be used so that a portion of fluid in the system can flow or diffuse through the space between the opening 56 and the lumen device 46, but a large portion of the fluid flows through the lumen of the lumen device 46, and the lumen device 46 is still held in position by the opening 56 during agitation. Loose-fitting will provide a opportunity to clean/sterilize the outer surface area of the lumen device 46 which is otherwise obscured by the opening 56.

A cleaning solution is then introduced into the container 2 and the enclosure 50 through fluid port 6a and 6b, respectively. The liquid level in the container 2 and the enclosure 50 is preferably not higher than the position of the vacuum port 32. A stirrer, a water jet or an air jet can be used to facilitate the cleaning of the outer surface of the lumen device 46. The cleaning solution is also circulated between container 2 and enclosure 50 through the lumen of the lumen device 46. There are at least two ways to make the circulation. One method is to apply vacuum to the enclosure 50 through second vacuum port 70 of vacuum chamber 66 and vacuum port 32 of the enclosure 50 while keeping vacuum chamber 66 and container 2 at atmospheric pressure or any pressure higher than that of the enclosure 50. This can be done similarly when vacuum chamber 66 is not used. The cleaning fluid then flows from the container 2 into the enclosure 50 through the lumen device 46. The liquid pump 54 circulates the cleaning fluid back to the container 2. The opening 56 and the stirrer 20 can be controlled by the electronic signals from the system. Air bubbles generated from air pump 10 can be introduced at this stage to enhance the scrubbing action during cleaning. Thus, both the outer surface and the inner surface of the lumen device 46 can be cleaned at the same time. Vacuum can be applied to container 2 to generate a pressure in the container 2 lower than that of the enclosure 50. Forced air also can be used to push liquid through the lumen. If desired, the interior and the exterior of the lumen device can be cleaned separately. The cleaning fluid can be removed from the container 2 and enclosure 50 through the fluid port 6a and 6b on the sloped bottom wall 4a and 4b. The cleaning fluid in the lumen device 46 can be removed either with vacuum or forced-air.

The rinsing with water and the treatment with liquid sterilant can be conducted similarly. When the treatment with a liquid sterilant is complete, the liquid sterilant is drained and a predetermined amount of the liquid sterilant can be retained in the wells. Then vacuum is applied to chamber 66 and container 2 either through vacuum port 68 or 70, or both in a manner described earlier. At least in certain stage, the vacuum should be high enough (or the pressure low enough) to vaporize the remaining sterilant in container 2 to sterilize and dry the device simultaneously. A plasma can be used as an option to enhance the efficacy and/or to remove the sterilant residual. After the sterilization is completed, the chamber is vented and the container is ready to be retrieved from the chamber. If desired, valve 35 can be closed at any pressure below the atmospheric pressure and the sterilized device is kept in container 2 under a subatmospheric pressure. This may serve as an indication of a well maintained sterility, i.e. if the vacuum still exists when container is opened after a period of time of storage that indicates the sterility of the sterilized device is well kept. The pressure can be monitored and controlled by the pressure sensor on the vacuum chamber 66 or in container 2.

Figure 5B:
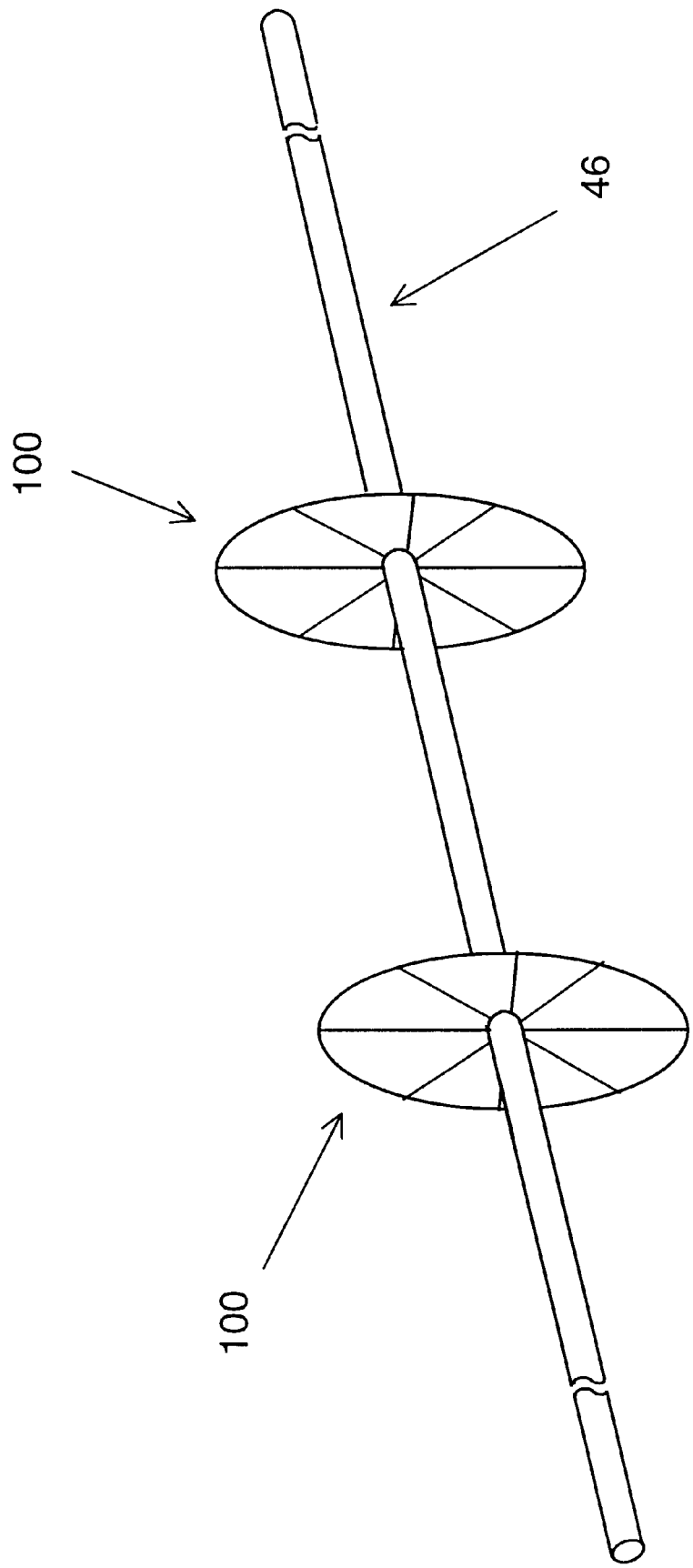

FIG. 5a shows a container very similar to that shown in FIG. 3a except that two holders 100 are used in opening 56 of interface 52. As shown in FIGS. 5a and 5b, the two holders 100 are secured to opening 56 along lumen device 46 or the passage of opening 56. Each holder 100 is sealed to opening 56 in any suitable conventional manner and each holder 100 is independently controllable. Holder 100 can be a shutter as the shutter described with FIGS. 3b and 3c, or made of two plates as described with FIGS. 3d–3g. FIG. 5b shows two holders 100 of shutter type holding a lumen device 46. During cleaning or sterilizing operation, a first holder 100 is first closed and a second holder 100 is opened, then the first holder is opened and the second holder 100 is closed. Thus, enclosures 50a and 50b are always separated or insulated from each other through the engagement of one holder 100 with the device 46 and, in the meantime, the two contact surface areas of the device 46 occluded by the two holders 100 are exposed alternately.

FIG. 5c shows two holders 100 of plate type holding a lumen device 46. Each of holders 100 can be constructed in the way as described previously with FIGS. 3d–3g. Preferably, the gap (the opening for passing the lumen device) formed between the two plates of one holder 100 forms an angle with that of the other holder 100 of the two holder structure. Preferably, the angle is 90 degree as shown in FIG. 5c. The two holders 100 are preferably positioned close enough so that when the expandable material 60 lined in the gap (opening) is expanded, the expandable material 60 will also expand outwardly away from the two plates and become in contact with the other holder 100, thus help seal the gap of the other holder 100. This configuration provides an advantage that no complete seal is needed for a single holder, yet a good seal such as a gas-tight seal can be achieved when two such holders are combined. It has been noted by the applicants that, when a cylindrical lumen device is placed across the gap between the two plates of holder 100, areas on the outer surface of the lumen device, where the diameter of the cylindrical lumen device is parallel to the gap, are more difficult to seal because the expandable material 60 has to expand extra distance to cover those areas. By providing two closely positioned holders 100 with the two gaps forming an angle, the above mentioned areas in each of the two holders can be sealed by the other holder. Therefore, the requirement to the expandable material can be lowered without sacrificing the sealing characteristics.

Figure 5D:
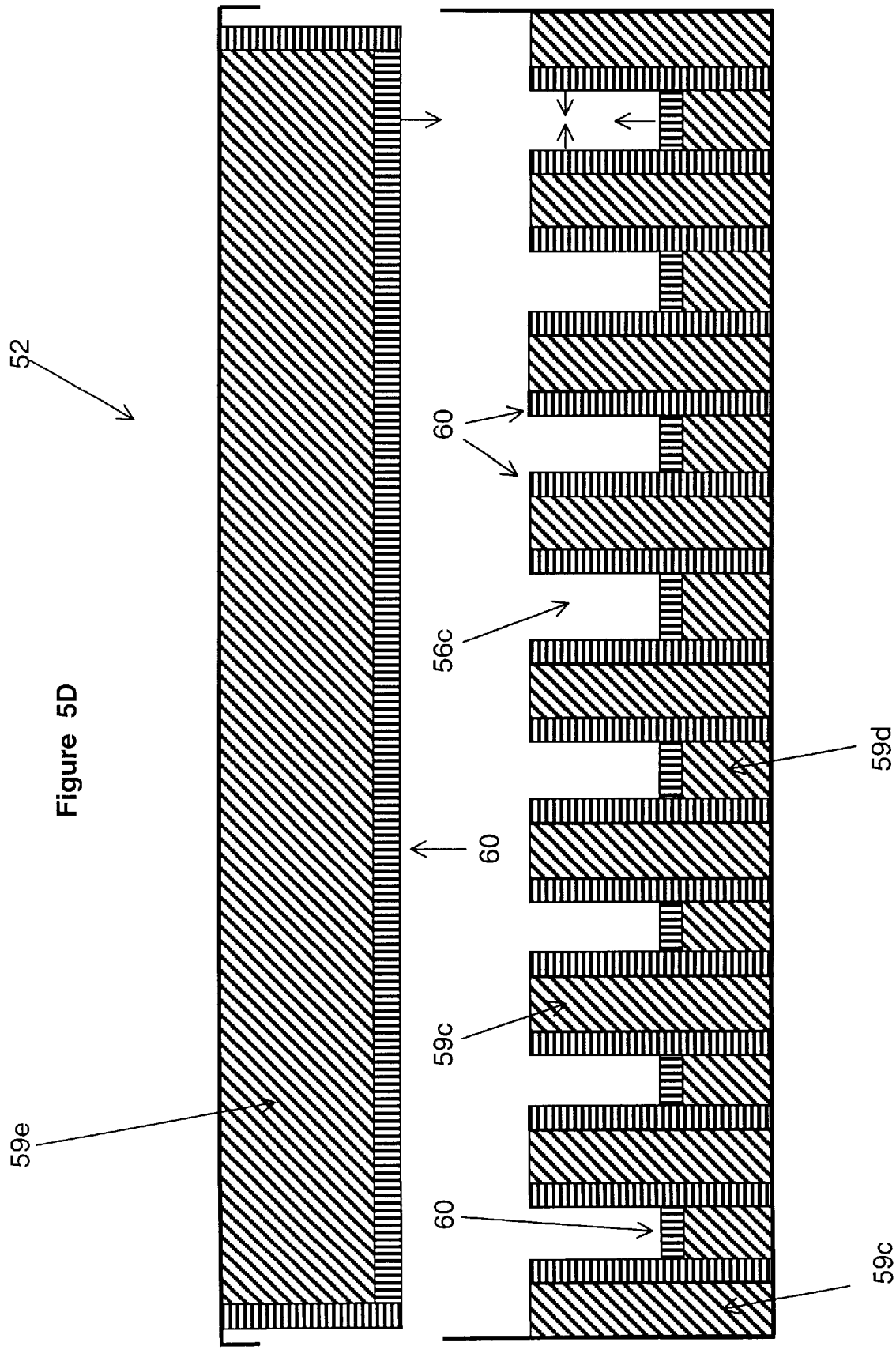
FIG. 5d is a schematic diagram of an interface of a container with multiple openings.

FIG. 5d shows another embodiment of an interface of the present invention. In this embodiment, the interface 52 contains multiple openings 56c. This interface 52 may have three parts. A first plate 59c has a plurality of openings 56c thereon. The cross section of the opening 56c as viewed from a direction perpendicular to the surface of plate 59c has an elongate shape with its longitudinal axis extending along a substantially vertical direction. Other orientation also can be adopted. Preferably, opening 56c has a rectangular cross section. The upper side of the openings 56c can be made open for easy access to a lumen device. The contact surface of opening 56c is provided with a layer of expandable material 60. A second plate 59d is positioned beside the first plate 59c in parallel. Plate 59d can be secured and sealed to the bottom and side walls of container 2 with its upper edge or surface equipped with a layer of expandable material 60. A third plate 59e is located above and aligned with second plate 59d. The third plate can be made a part of the lid for container 2. The lower edge of plate 59e and the upper edge of plate 59d form a gap for passing a lumen device. The edges of the third plate is also provided with a layer of expandable or other sealing material 60. Preferably, the second plate 59d and the third plate 59e lie in one vertical plane, and the first plate 59c lies in another vertical plane parallel to that containing second plate 59d and third plate 59e. Preferably, the gap formed between plate 59d and 59e forms an angle with openings 56c, more preferably the angle is a right angle. In one preferred embodiment, the gap between second plate 59d and third plate 59e has a horizontal orientation, and the openings 56c have a vertical orientation. The distance between the first plate 59c and the second and third plate 59d and 59e can be adjusted depending on intended purpose. Preferably, they are closely positioned relative to each other so that when the expandable material 60 on one plate is expanded, it will become in contact with the other plate to further facilitate seal around the lumen device passing both the gap between plate 59d and 59e and the opening 56c of plate 59c. Preferably, the dimension and the expandable material layer of opening 56c is determined to allow the opening 56c to be closed and sealed when the expandable material is expanded even no lumen device is placed through the opening.

Figure 6:
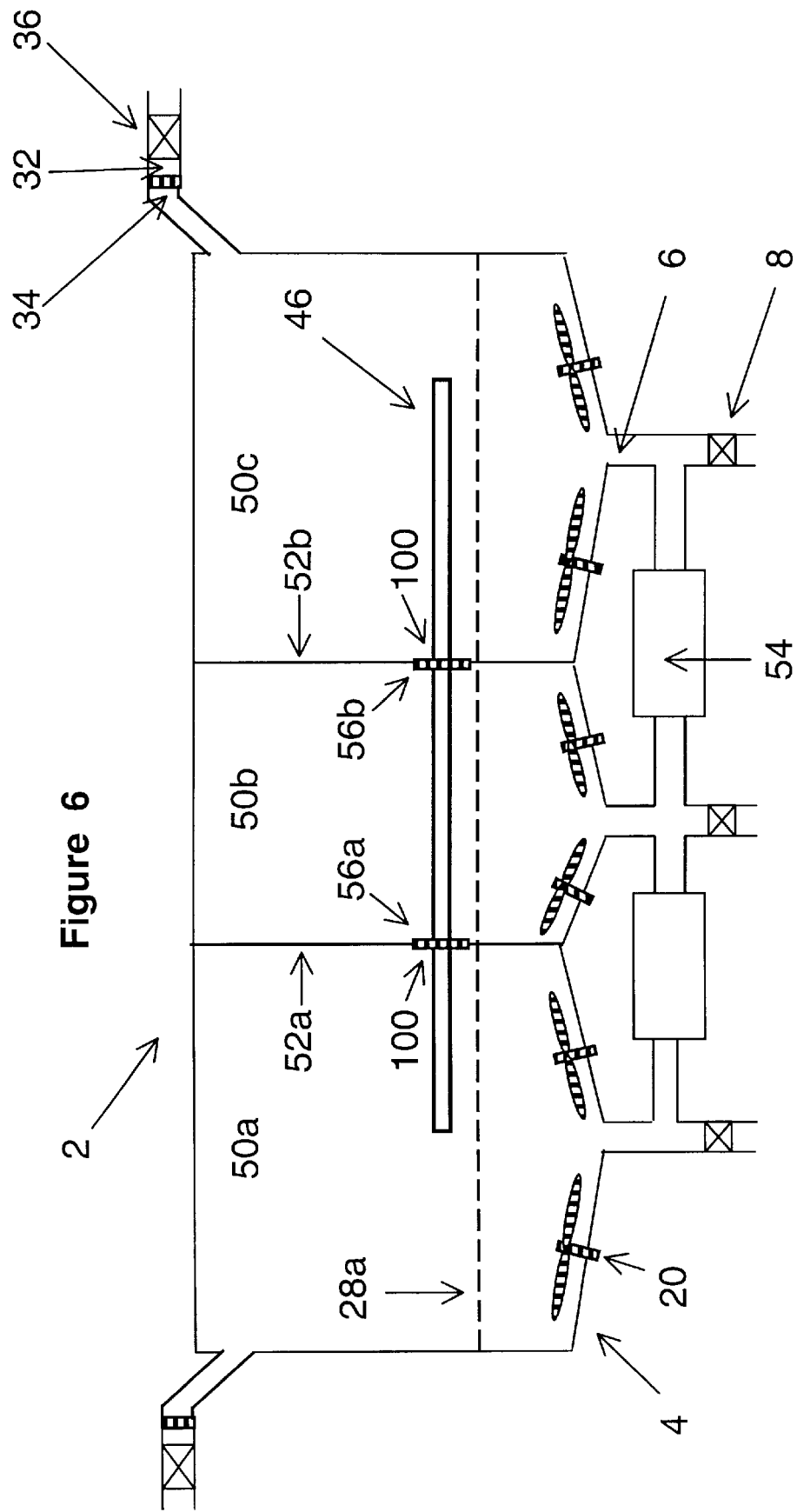
FIG. 6 is a schematic diagram of a container separated into three enclosures by two interfaces according to the present invention.

FIG. 6 shows a container 2 has three enclosures 50a, 50b, and 50c separated by two interfaces 52a and 52b, respectively. Enclosure 50b is located in between and shares interfaces 52a and 52b with enclosure 50a and 50c. Other parts of the container 2 of FIG. 6 are similar to those of the container shown in FIG. 3a, and they are indicated by same numerical references. Two openings 56a and 56b are located in interface 52a and 52b, respectively. Two holders 100 are also location in interface 52a and 52b. Opening 56a and 56b can be of any form as discussed previously. In practice of the process of the present invention, a lumen device 46 is placed across both opening 56a and opening 56b with one end located in enclosure 50a and the other end in enclosure 50c. The advantage of the configuration is to help obtain a large pressure drop between the two ends of the device 46. Under certain circumstances, the seal between the opening and the lumen device may be not gas-tight, thus it is difficult to keep a large pressure drop at the two sides of the interface with such a seal. By adding one intermediate enclosure 50b, the pressure drop across each interface 52a and 52b can be kept at a relative low level, yet the total pressure between the two ends of the device 46 or, in other words, between enclosure 50a and enclosure 50c can be still large enough to generate desired flow rate through the lumen of the lumen device 46. If desired, one interface 52a or 52b can be removed or opened, and in those cases the container 2 can be operated just like that of FIG. 3a.

Figure 7A:
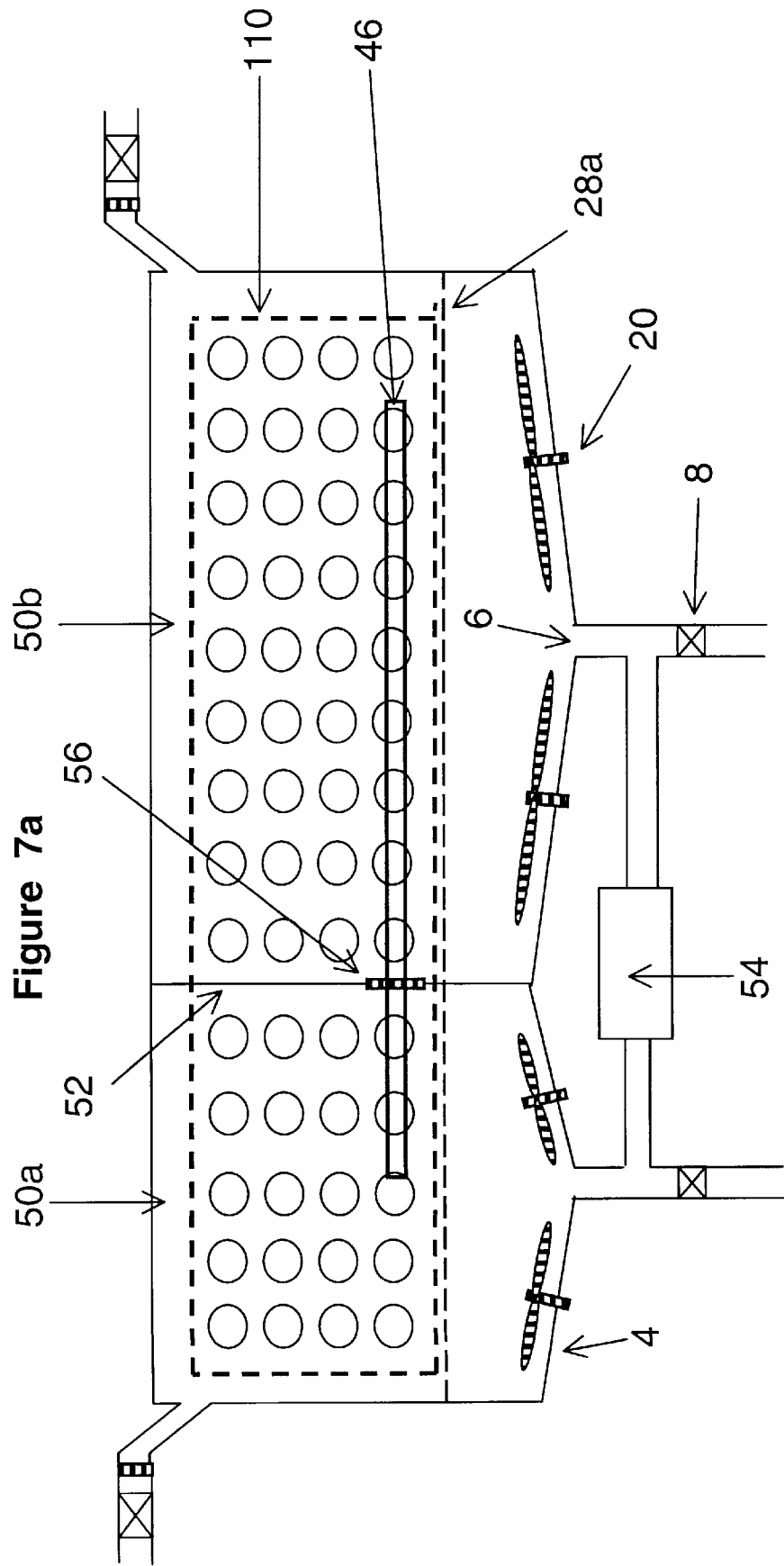
FIG. 7a is a schematic diagram of a container having an interface and a tray across the interface according to the present invention.
Figure 8A:
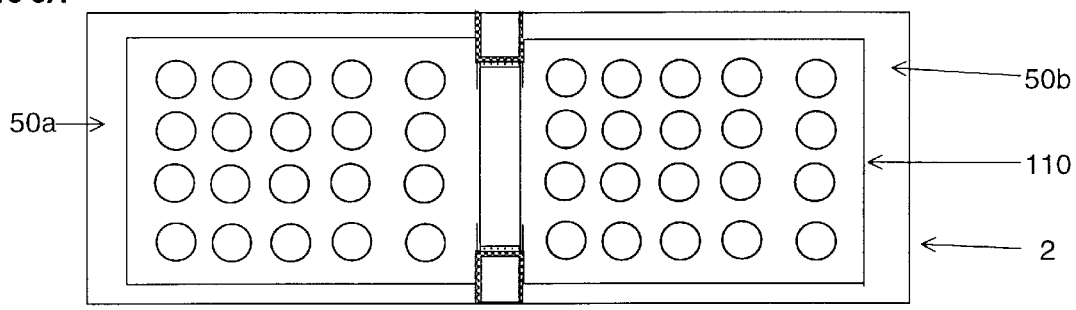
Figure 8B:
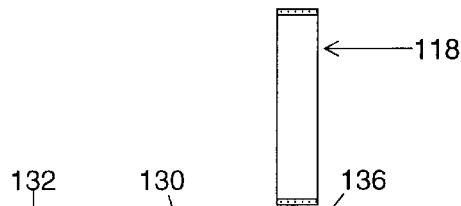
Figure 8C:
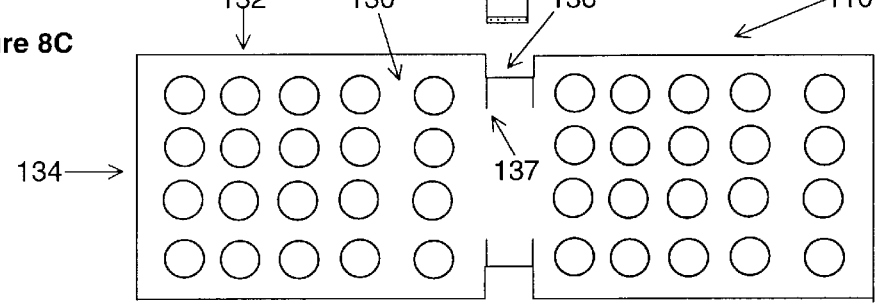
Figure 8D:
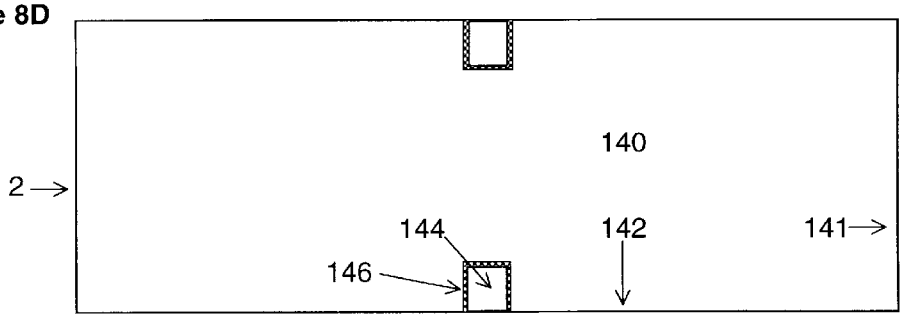
FIG. 8d is a top view of the container of FIG. 7a without the tray and the interface.

FIG. 7a shows a container 2 separated into an enclosure 50a and an enclosure 50b by an interface 52 similar to the container of FIG. 3a except that a tray 110 is placed across interface 52 and located in both enclosure 50a and enclosure 50b. The tray 110 shown in FIG. 7a has a rectangular shape with four side walls perpendicular to a bottom wall defining a space for receiving a lumen device 46. The side and bottom walls have open holes thereon. As shown in FIG. 7b, interface 52 can be configured to have two parts. The first part forms a tray seat 112 extending along an interior periphery of container 2. Tray seat 112 has a first edge secured and sealed to the interior periphery of container 2 and a second edge 114 shaped to receive tray 110. Edge 114 has a bottom portion and two side portions defining an open rectangular cross section. On top of edge 114 is a sealing layer 116 made of expandable, compressible, or other suitable material. When tray 110 is placed into container 2, an exterior periphery of tray 110 will seat on edge 114 and layer 116. The second part of interface 52 can be a removable plate 118 having an edge 120 shaped to fit the shape of an interior periphery of tray 110. On top of edge 120 is a sealing layer 122 made of expandable, compressible, or other suitable material. Plate 118 is inserted into tray 110 along an interior periphery of tray 110. A guide rail can be provided with tray 110 to guide plate 118 moving along an predetermined interior periphery. Different shapes can be used for edge 114 of seat 112 and edge 120 of plate 118, as long as the shape matches that of the exterior and interior periphery of tray 110. For example, in one embodiment, the open rectangular formed by edge 114 and edge 120 shown in FIG. 7b is modified by making the upper edge longer than the bottom edge of the open rectangular and tray 110 has a corresponding shape. This configuration makes it easier to the plate 118 down into tray 110 and seal it. Plate 118 can further include an opening 56 of any kind as discussed previously with FIGS. 3b–3g. Opening 56 can be located in plate 118 or on edge 120 facing the bottom of tray 110 where lumen device is placed. In one embodiment, a layer of expandable, compressible, or other suitable sealing material is also provided with tray 110 along the interior periphery where plate 118 is inserted. FIG. 7c shows another embodiment in which tray 110 has a partition 111 therein. Partition 111 can be made as part of the tray 110. Upper edge 111a of partition 111 has a layer of expandable, compressible, or other suitable sealing material. Partition 111 is aligned with plate 118 so that when plate 118 is inserted into tray 110 seal can achieved between upper edge 111a of partition 111 and lower edge of plate 118, and a lumen device can be placed through the gap or opening 56 formed between upper edge 111a of partition 111 and lower edge of plate 118. In one embodiment, in the contact area between tray 110 and interface 52 (or plate 112 and 118), a portion of side and bottom walls of tray 110 is removed so that in those portion the sealing layer 116 of tray seat 112 and the sealing layer 122 of plate 118 of the interface 52 are in direct contact. Plate 118 can be secured to a lid or cover 119 for container 2 and, a portion of the lower surface of the cover 119 is provided with a layer of expandable, compressible, or other suitable sealing material to seal the upper edge of the tray 110 and the container 2 as shown in FIG. 7c.

When exposed to a pressure difference between enclosure 50a and 50b, tray 110 may be forced to move from high pressure side to low pressure side. In order to prevent this from happening, a stopper mechanism is provided. In one embodiment as shown in FIGS. 8a–8d which are top views of container 2 and tray 110, tray 110 has a rectangular bottom wall 130 with two side walls 132 along two longer edges of bottom wall 130 and two side walls 134 along two shorter edges of bottom wall 130. There is an indentation on each side wall 132 extending along the entire height of side wall 132 and substantially perpendicular to bottom wall 130. Container 2 also has a rectangular bottom wall 140 with two side walls 142 along the two longer edges of bottom wall 140 and two side walls 141 along two shorter edges of bottom wall 140. There is a projection 144 on each side wall 142 extending along the entire height of side wall 142 and perpendicular to bottom wall 140. The surface of projection 144 is covered with a layer of expandable, compressible, or other suitable sealing material 146. The projection 144 has a shape matching that of the indentation 136. When tray 110 is placed into container 2, indentation 136 will engage with projection 146 so as to hold tray 110 in position. A tray seat 112 with a layer of sealing material on its upper surface is provided on bottom wall 140 of container 2 extending between two projections 146. Tray 110 also has two edges 137 on each side wall 132 extending inwardly from indentation 136. A removable plate 118 with a layer of sealing material on its contact edge is inserted into tray 110 through a rail defined by extruding edge 137. In another embodiment, each side wall 141 is provided with a stopper, such as an extrusion, to confine the movement of tray 110 along a direction perpendicular to interface 52.

Figure 9:
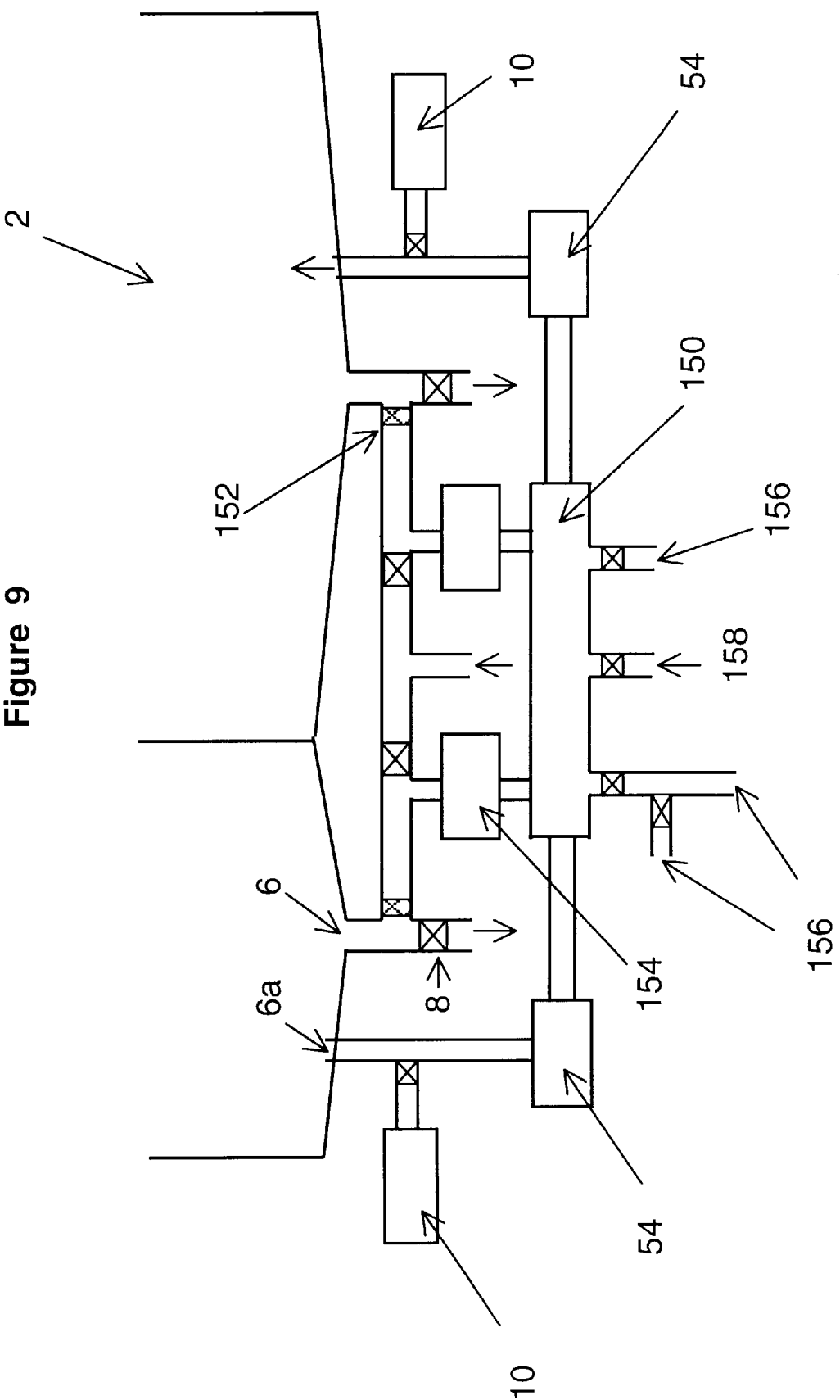
FIG. 9 is a schematic diagram showing a recycle system for processing liquid.

FIG. 9 shows a recycling system which can be incorporated into any container systems used in the present invention. In this system, used liquid in a cleaning/sterilizing process is drained or pumped to a reservoir 150 through a filter 152. A pump 154 can be provided between reservoir 150 and fluid port 6 to help drain the used liquid into reservoir 150. The filtered liquid in reservoir 150 can be then cycled back to container 2 through a fluid port 6a. If necessary, filter 152 can be cleaned by back flash. Reservoir 150 is also equipped with several inlets 156 for water, cleaning chemical, and sterilant, respectively, and a drain 158.

The present invention has been described above. Many modifications and variation of the cleaning/sterilizing or cleaning/disinfecting process and the apparatus in such process may be made without departing substantially from the spirit and scope of the present invention. Accordingly, it should be clearly understood that the form of the invention described and illustrated herein is exemplary only, and is not intended as a limitation on the scope.

What is claimed is:

1. A method for cleaning/sterilizing or cleaning/disinfecting a device having a lumen with at least two open ends comprising the steps of:
    a) providing a container having at least one enclosure and at least one interface separating said enclosure from said container, said interface having at least one opening thereon;
    b) placing said device across said opening with one open end in said container and another open end in said enclosure;
    c) generating a flow of a cleaning solution through said lumen to clean the inner surface of said lumen;
    d) generating a flow of rinse solution through said lumen to rinse the inner surface of said lumen;
    e) treating said device with a chemical germicide; and
    f) adjusting said opening in any of steps c) to e) to reduce areas on outer surface of said device which are occluded, by contact with the opening, from exposure to the cleaning solution, the rinse solution, or the chemical germicide, or to expose said areas to the cleaning solution, the rinse solution, or the chemical germicide.

2. A method of claim 1, wherein one or more steps are repeated.

3. A method of claim 1, wherein, along its passage, said opening has at least two independently controllable apertures for holding and sealing said device.

4. A method of claim 3, wherein the step of adjusting said opening comprises opening one of said two apertures while closing the other aperture so that the areas on the outer surface of said device occluded by the two apertures are alternately exposed to the cleaning solution, the rinse solution, or the chemical germicide in step c), d), or e), respectively.

5. A method of claim 1, further comprising retaining a predetermined amount of said chemical germicide in said container and enclosure and vaporizing the retained chemical germicide to sterilize, or disinfect, and dry said device under vacuum during or after step e).

6. A method of claim 5, wherein the sterilizing or disinfecting is conducted under a diffusion restricted environment.

7. A method of claim 5, wherein the sterilizing or disinfecting is conducted by reducing pressure to a first predetermined pressure followed by further reducing said first pressure to a predetermined second pressure.

8. A method of claim 5, wherein the sterilizing or disinfecting is conducted at controlled pump down rate.

9. A method of claim 5, wherein the sterility of said device is maintained in the container and enclosure after said device is sterilized and dried.

10. A method of claim 5, further comprising removably attaching said container to a vacuum system for applying vacuum to said container or enclosure and detaching said container after the device is sterilized, or disinfected, and dried.

11. A method of claim 1, wherein the flow through said lumen is generated by applying a pressure higher than atmospheric pressure at one end of said lumen, or by applying vacuum to one end of said lumen device.

12. A method of claim 1, further comprising treating a non-lumen device in said container or enclosure.

13. A method of claim 1, wherein said opening has separately controllable and moveable contact points, and the adjusting step comprises controlling said contact points so that a different portion of said contact points is made in contact with the device alternately.

14. A method of claim 1, wherein the opening forms a seal around said device selected from the group consisting of a gas-tight seal, a tight-fitting seal, or a loose-fitting seal.

15. An apparatus for cleaning/sterilizing or cleaning/disinfecting a lumen device having at least two open ends comprising:
a container having a fluid port for flowing and draining a fluid in and out said container;
at least one enclosure coupled with said container for receiving part of the lumen device so that one end of said lumen device is located in said enclosure and the other end of said lumen device is located in said container;
an interface separating said container and enclosure, said interface having at least one opening;
at least one openable and closeable holder sealably coupled to said opening, said holder being openable and closeable without opening said container or enclosure;
a source for creating a pressure difference between said two open ends to generate a flow through the lumen of said lumen device;
a cleaning mechanism adapted to clean said device in said container or said enclosure.

16. An apparatus of claim 15, wherein said interface is removable.

17. An apparatus of claim 15, wherein said holder is a shutter.

18. An apparatus of claim 15, wherein said holder is equipped with expandable material on its contact surface with said device.

19. An apparatus of claim 15, wherein said holder is equipped with compressible material on its contact surface with said device.

20. An apparatus of claim 15, wherein said apparatus further comprises a vacuum system, said container comprises a gas-permeable and microorganism-impermeable barrier and is detachably coupled to said vacuum system.

21. An apparatus of claim 20, wherein said gas-permeable and microorganism-impermeable barrier is equipped with a valve for opening and closing gas communication between the container and the vacuum system or between the container and atmosphere through said barrier.

22. An apparatus of claim 15, wherein said cleaning mechanism is selected from the group consisting of a stirrer, a liquid jet, an air jet, ultrasonics, or a bubble generator.

23. An apparatus of claim 15, wherein said container has a first enclosure sharing with the container a first interface having a first opening and a second enclosure sharing with the first enclosure a second interface having a second opening, wherein the device is placed across the first and second interface through the first and second opening so that one open end of the device is located in the container and the other open end of the device is located in the second enclosure.

24. An apparatus for cleaning/sterilizing or cleaning/disinfecting a lumen device having at least two open ends comprising:
a container having a fluid port for flowing and draining a fluid in and out said container;
at least one enclosure coupled with said container for receiving part of the lumen device so that one end of said lumen device is located in said enclosure and the other end of said lumen device is located in said container;
an interface separating said container and enclosure, said interface having at least one opening;
at least one openable and closeable holder sealably coupled to said opening, wherein said holder has two plates forming a gap therebetween for passing said device, the surfaces of the plates facing the gap are equipped with expandable or compressible material;
a source for creating a pressure difference between said two open ends to generate a flow through the lumen of said lumen device;
a cleaning mechanism adapted to clean said device in said container or said enclosure.

25. An apparatus for cleaning/sterilizing or cleaning/disinfecting a lumen device having at least two open ends comprising:
a container having a fluid port for flowing and draining a fluid in and out said container;
at least one enclosure coupled with said container for receiving part of the lumen device so that one end of said lumen device is located in said enclosure and the other end of said lumen device is located in said container;
an interface separating said container and enclosure, said interface having at least one opening;
at least one openable and closeable holder sealably coupled to said opening, wherein two independently controllable holders are sealably arranged along the passage of at least one opening;
a source for creating a pressure difference between said two open ends to generate a flow through the lumen of said lumen device;
a cleaning mechanism adapted to clean said device in said container or said enclosure.

26. An apparatus of claim 25, wherein each one of the two holders comprises two plates forming a gap therebetween for passing said device, the surfaces of the plates facing the gap are equipped with expandable or compressible material.

27. An apparatus of claim 26, wherein each of said gaps defines an elongate cross section having a longitudinal axis as viewed from a direction perpendicular to the surface of said plates, the longitudinal axis of one said gap forms an angle with that of the other gap, and said two holders are placed close enough to each other for said expandable material on one holder to be brought in contact with the other holder when the expandable material is expanded.

28. An apparatus of claim 25, wherein said holder comprises a shutter.

29. An apparatus for cleaning/sterilizing or cleaning/disinfecting a lumen device having at least two open ends comprising:

a container having a fluid port for flowing and draining a fluid in and out said container;

at least one enclosure coupled with said container for receiving part of the lumen device so that one end of said lumen device is located in said enclosure and the other end of said lumen device is located in said container;

an interface separating said container and enclosure, said interface having at least one opening, wherein said interface comprises a first plate having a plurality of openings with elongate cross section, and at least two other plates forming a gap along a longitudinal direction, said plates are configured so that the longitudinal direction of the gap and the longitudinal direction of the elongate cross section of the opening form a substantially right angles;

at least one openable and closeable holder sealably coupled to said opening, a source for creating a pressure difference between said two open ends to generate a flow through the lumen of said lumen device;

a cleaning mechanism adapted to clean said device in said container or said enclosure.

30. An apparatus for cleaning/sterilizing or cleaning disinfecting a lumen device having at least two open ends comprising:

a container having a fluid port for flowing and draining a fluid in and out said container;

at least one enclosure coupled with said container for receiving part of the lumen device so that one end of said lumen device is located in said enclosure and the other end of said lumen device is located in said container;

an interface separating said container and enclosure, said interface having at least one opening;

at least one openable and closeable holder sealably coupled to said opening, wherein said holder has a plurality of contact points on its inner surface for holding the device, said contact points being separately controllable and moveable;

a source for creating a pressure difference between said two open ends to generate a flow through the lumen of said lumen device;

a cleaning mechanism adapted to clean said device in said container or said enclosure.

* * * * *